US009790203B2

(12) United States Patent
Geneste et al.

(10) Patent No.: US 9,790,203 B2
(45) Date of Patent: Oct. 17, 2017

(54) INHIBITOR COMPOUNDS OF PHOSPHODIESTERASE TYPE 10A

(71) Applicants: ABBVIE DEUTSCHLAND GMBH & CO. KG, Wiesbaden (DE); ABBVIE INC., North Chicago, IL (US)

(72) Inventors: Hervé Geneste, Wiesbaden (DE); Sean Colm Turner, Wiesbaden (DE); Michael Ochse, Wiesbaden (DE); Karla Drescher, Wiesbaden (DE); Lawrence A. Black, North Chicago, IL (US); Katja Jantos, Wiesbaden (DE)

(73) Assignees: ABBVIE INC., North Chicago, IL (US); ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

(21) Appl. No.: 14/087,680

(22) Filed: Nov. 22, 2013

(65) Prior Publication Data
US 2014/0148461 A1    May 29, 2014

Related U.S. Application Data

(60) Provisional application No. 61/729,877, filed on Nov. 26, 2012.

(51) Int. Cl.
| C07D 401/14 | (2006.01) |
| C07D 401/04 | (2006.01) |
| C07D 401/10 | (2006.01) |
| C07D 471/04 | (2006.01) |
| C07D 487/04 | (2006.01) |

(52) U.S. Cl.
CPC ......... *C07D 401/14* (2013.01); *C07D 401/04* (2013.01); *C07D 401/10* (2013.01); *C07D 471/04* (2013.01); *C07D 487/04* (2013.01)

(58) Field of Classification Search
None
See application file for complete search history.

(56) References Cited

U.S. PATENT DOCUMENTS

| 2007/0155779 A1 | 7/2007 | Verhoest et al. |
| 2013/0158031 A1 | 6/2013 | Cai et al. |

FOREIGN PATENT DOCUMENTS

| EP | 1104758 A1 * | 6/2001 | ........... C07D 231/12 |
| WO | 03/093499 | 11/2003 | |
| WO | 2005/012485 | 2/2005 | |
| WO | 2005/120514 | 12/2005 | |
| WO | 2006/028957 | 3/2006 | |
| WO | 2006/072828 | 7/2006 | |
| WO | 2007/022280 | 2/2007 | |
| WO | 2007/082546 | 7/2007 | |
| WO | 2007/085954 | 8/2007 | |
| WO | 2007/096743 | 8/2007 | |
| WO | 2007/098169 | 8/2007 | |
| WO | 2007/098214 | 8/2007 | |
| WO | 2007/100880 | 9/2007 | |
| WO | 2007/103370 | 9/2007 | |
| WO | 2007/103554 | 9/2007 | |
| WO | 2007/137819 | 12/2007 | |
| WO | 2007/137820 | 12/2007 | |
| WO | 2008/001182 | 1/2008 | |
| WO | 2008/004117 | 1/2008 | |
| WO | 2008/006372 | 1/2008 | |
| WO | 2008/020302 | 2/2008 | |
| WO | 2009/025823 | 2/2009 | |
| WO | 2009/025839 | 2/2009 | |
| WO | 2009/029214 | 3/2009 | |
| WO | 2009/036766 | 3/2009 | |
| WO | 2009/068246 | 6/2009 | |
| WO | 2009/068320 | 6/2009 | |
| WO | 2009/070583 | 6/2009 | |
| WO | 2009/070584 | 6/2009 | |
| WO | 2010/054260 | 5/2010 | |
| WO | 2011/008597 | 1/2011 | |
| WO | 2011/051324 | 5/2011 | |
| WO | 2011/072694 | 6/2011 | |
| WO | 2012/062319 | 5/2012 | |
| WO | 2012/064603 | 5/2012 | |
| WO | 2012/112918 | 8/2012 | |

OTHER PUBLICATIONS

Dorwald, F.A., Side Reactions in Organic Synthesis, 2005, Wiley: VCH, Weinheim, p. IX.*
Danziger, Automated Site-Directed Drug Design: A General Algorithm for Knowledge Acquisition about Hydrogen-Bonding Regions at Protein Surfaces, Proceedings of the Royal Society of London. Series B, Biological Sciences, 1989, 236(1283), pp. 101-113.*
International Search Report & Written Opinion for Application No. PCT/EP2013/074532 dated Mar. 13, 2014 (11 pages).
Alexander et al., "(Acyloxy)alkyl carbamates as novel bioreversible prodrugs for amines: increased permeation through biological membranes," J. Medicinal Chem. 1988, 31(2), 318-322.
Bourrain et al., Synlett. 5 (2004), 795-798.
Braña et al., Journal of Heterocyclic Chemistry 18 (7), 1305-1308 (1981).
Burns et al., "PET ligands for assessing receptor occupancy in vivo," Annual Reports in Medicinal Chemistry 36 (2001) pp. 267-276.
Burns et al., "Positron emission tomography neuroreceptor imaging as a tool in drug discovery, research and development," Current Opinion in Chemical Biology 3(4), (1999) 388-394.
Cantin et al., Bioorganic & Medicinal Chemistry Letters 17 (2007) 2869-2873.
Chappie et al., Current Opinion in Drug Discovery & Development 12(4), (2009) 458-467.

(Continued)

Primary Examiner — Kathrien Cruz
Assistant Examiner — Andrew Lee
(74) Attorney, Agent, or Firm — Neal, Gerber & Eisenberg LLP

(57) ABSTRACT

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

26 Claims, No Drawings

(56) References Cited

OTHER PUBLICATIONS

Di, The Society for Biomolecular Screening, 2003, 453-462.
Diaz et al., Journal of Pharmacological and Toxicological Methods, 50 (2004), 187-199.
Eluguero et al., Synthesis 1997, 5, 563-566.
Francis et al., Physiol. Rev., 91 (2011) 651-690.
Grauer et al., Journal of Pharmacology and Experimental Therapeutics, DOI 10.1124 JPET 109.155994 (2009).
Hietala, "Ligand-receptor interactions as studied by PET: inplications for Drug development," Annals of Medicine (Helsinki) 31(6), (1999), pp. 438-443.
Kurtan et al., Journal of the American Chemical Society 123(25), 5962-5973 (2001).
Nishi, The Journal of Neuroscience 2008, 28, 10460-10471.
Obach, DMD, 1999, vol. 27, N. 11, 1350-1359.
Prabakaran et al., Tetahedron Lett. 52 (2011) 2566-2570.
Rodefer et al., Eur. J. Neurosci., 4 (2005) 1070-1076.
Schmidt et al., The Journal of Pharmacology and Experimental Therapeutics 325 (2008) 681-690.
Seeger et al., Brain Research, 2003, 985, 113-126.
Lee et al., Bioorg. Med. Chem. Lett. 2001, 9, 3243-3253.
Sotty et al., J. Neurochem., 109 (2009) 766-775.
Stille et al., Angew. Chem. Int. Ed. Engl. 1986, 25, 508.
Suzuki et al., Chem. Rev. 1995, 95, 2457-2483.
Varney et al., Journal of Medicinal Chemistry 38(11), 1892-1903 (1995).
Wermuth, The Practice of Medicinal Chemistry, 1996, pp. 671-715.
Yang et al., J. Med. Chem. 2004, 47(6), 1547-1552.
Zhang et al., Tetrahedron Lett., 52 (2011), 311-313.
Zhe et al., J. Med. Chem. 2005, 48(5), 1596-1609.
Hoefgen et al., Targeting PDE10A in Schizophrenia, Drugs of the Future 2012, 37(8), 577-589.
Blokland et al., PDE Inhibition and cognition enhancement, Expert Opin. Ther. Patents 2012, 22(4), 349-354.
Langen et al., Effect of PDE10A inhibitors on MK-801-induced immobility in the forced swim test, Psychopharmacology, 2011, DOI 10.1007/s00213-011-2567-y.
Kehler et al., PDE10A Inhibitors: Novel Therapeutic Drugs for Schizophrenia, Current Pharmaceutical Design 2011, 17, 137-150.
Kerner et al., Genome-Wide Association Study in Bipolar Patients Stratified by Co-Morbidity, PLoS ONE, 2011, 6(12), e28477.
Garcia-Osta et al., Phosphodiesterases as Therapeutic Targets for Alzheimer's Disease, ACS Chemical Neuroscience Nov. 21, 2012; 3(11): 832-844.
Search Report for SG Application No. 11201540115X dated Mar. 3, 2016.
Danziger, D. J., and Dean, P. M., "Automated Site-Directed Drug Design: A General Algorithm for Knowledge Acquisition About Hydrogen-Bonding Regions at Protein Surfaces," Proceedings of the Royal Society of London B: Biological Sciences, 1989, vol. 236(1283), pp. 101-113.
Cannon J.G., "Analog Design," in: Burger's Medicinal Chemistry and Drug Discovery, 1995, Fifth Edition, vol. I: Principles and Practice, Wolf M.E., Ed., John Wiley and Sons, Inc., New York, pp. 783-802.
Dorwald F.Z., "Side Reactions in Organic Synthesis—a Guid to Successful Synthesis Design," 2005, pp. 9-16.
International Preliminary Report on Patentability for Application No. PCT/EP2013/074532, mailed on Jun. 4, 2015, 9 pages.
Sheridan R.P., "The Most Common Chemical Replacement in Drug-Like Compounds," Journal of Chemical Information and Computer Sciences, 2002, vol. 42 (1), pp. 103-108.
Zheng G.Z., et al., "Structure-Activity Relationship of Triazafluorenone Derivatives as Potent and Selective mGluR1 Antagonists," Jounal of Medical Chemistry, 2005, vol. 48 (23), pp. 7374-7388.

* cited by examiner

INHIBITOR COMPOUNDS OF PHOSPHODIESTERASE TYPE 10A

CROSS-REFERENCE TO RELATED APPLICATIONS

This claims priority to U.S. Patent Application No. 61/729,877, filed on Nov. 26, 2012, the contents of which are fully incorporated herein by reference.

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 113-126). Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-3yl]phenoxymethyl}-quinoline) and TP-10, i.e. 2-{4-[pyridine-4-yl-1-(2,2,2-trifluoroethyl)-1-H-pyrazol-3-3yl]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Imidazo[1,5-a]pyrido[3,2-e]pyridazines and structurally related tricyclic imidazo[1,5-a]pyridazines—see WO 2007/137819, WO 2007/137820, WO 2009/068246, WO 2009/068320, WO 2009/070583, WO 2009/070584, WO 010/054260 and WO 2011/008597;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214;

MP10 and MP10 like compounds: WO 2006/072828, WO 2008/001182 and WO 2008/004117; and benzodiazepines—see WO 2007/082546.

For a further review see also T. Chappie et al. Current Opinion in Drug Discovery & Development 12(4), (2009) 458-467) and the literature cited therein.

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodiesterases such as PDE2, PDE3 or PDE4;
ii. metabolic stability, in particular microsomal stability, e.g. measured in vitro, in liver microsomes from various species (e.g. rat or human) in human cells, such as hepatocytes;
iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;
iv. a suitable solubility in water (in mg/ml);
v. suitable pharmacokinetics (time course of the concentration of the compound of the invention in plasma or in tissue, for example brain). The pharmacokinetics can be described by the following parameters: half-life, volume of distribution (in $l \cdot kg^{-1}$), plasma clearance (in $l \cdot h^{-1} \cdot kg^{-1}$), AUC (area under the curve, area under the concentration-time curve (in $ng \cdot h^{-1} \cdot kg \cdot l^{-1}$), oral bioavailability, (the dose-normalized ratio of AUC after oral administration and AUC after intravenous administration), the so-called brain-plasma ratio (the ratio of AUC in brain tissue and AUC in plasma);
vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).
vii. high free fraction in brain, i.e. the fraction of the compound bound to proteins should be low.
viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal stability, cytosolic stability or hepatocyte stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

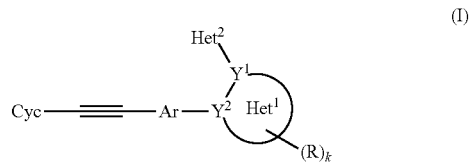

(I)

wherein
$Y^1$ and $Y^2$ are adjacent atoms in $Het^1$, which are independently selected from the group consisting of carbon and nitrogen;
k is 0, 1, 2 or 3;
$Het^1$ is a bivalent monocyclic 5- or 6-membered heteroaromatic radical, having 1, 2 or 3 heteroatoms or heteroatom moieties selected from O, S, N and N—$R^a$ as ring members, or a bivalent fused bicyclic 8-, 9- or 10-membered heteroaromatic radical, having 1, 2, 3 or 4 heteroatoms or heteroatom moieties selected from O, S, N and N—$R^a$ as ring members;
$Het^2$ is selected from the group consisting of
  i. saturated or partially unsaturated, 5- to 10-membered mono- or heterobicyclic radical, having 1, 2 or 3 heteroatoms or heteroatom moieties selected from O, S, S=O, S(=O)$_2$, N and N—$R^{1a}$ as ring members,
  ii. monocyclic 5- or 6-membered hetaryl, having 1, 2 or 3 heteroatoms or heteroatom moieties selected from O, S, N and N—$R^{1a}$ as ring members,
  iii. bicyclic 8-, 9- or 10-membered hetaryl, having 1, 2 or 3 heteroatoms or heteroatom moieties selected from O, S, N and N—$R^{1a}$ as ring members,
  iv. phenyl
  where $Het^2$ may carry 1, 2 or 3 radicals $R^1$;
Cyc is selected from
  i. monocyclic 5- or 6-membered hetaryl having 1 or 2 nitrogen atoms and optionally a further heteroatom selected from O, S and N as ring members, which is unsubstituted or may carry 1, 2, 3 or 4 identical or different substituents $R^2$,
  ii. fused 8-, 9- or 10-membered bicyclic hetaryl having one heteroatom selected from O, S and N and optionally 1, 2 or 3 nitrogen atoms as ring members, where the fused bicyclic hetaryl is unsubstituted or may carry 1, 2, 3 or 4 identical or different substituents $R^2$,
  iii. phenyl, which carries a monocyclic hetaryl radical having 1 or 2 nitrogen atoms and optionally a further heteroatom selected from O, S and N as ring members, which in addition to monocyclic hetaryl, may carry 1, 2 or 3 identical or different substituents $R^{2a}$, and iv. $C_5$-$C_8$-cycloalkyl or saturated or partially unsaturated, 5- to 10-membered heteromonocyclic or heterobicyclic radical, having 1, 2 or 3 heteroatoms or heteroatom moieties selected from O, S, S=O, S(=O)$_2$, N and N—$R^{1a}$ as ring members, and which may carry 1, 2 or 3 identical or different substituents $R^{2b}$, Ar phenylene or bivalent 6-membered hetaryl having 1, 2 or 3 nitrogen atoms as ring members, where phenylene and bivalent 6 membered hetaryl are unsubstituted or carry 1, 2, 3 or 4 identical or different substituents $R^3$, R is attached to a carbon atom of Het$^1$ and selected from the group consisting of halogen, CN, $NR^{13}R^{14}$, C(O)$NR^{13}R^{14}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $C_2$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^a$ is selected from the group consisting of hydrogen, C(O)$NR^{13}R^{14}$, $C_1$-$C_6$-alkyl, $C_2$-$C_6$-alkenyl, $C_2$-$C_6$-alkynyl, trimethylsilyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

two radicals R or the radical R together with the radical $R^a$, if attached to adjacent ring atoms, may also form linear $C_3$-$C_5$-alkanediyl, wherein 1 or 2 CH$_2$ moieties can be replaced by C=O, O, S, S(=O), S(=O)$_2$ or NR', and where alkanediyl is unsubstituted or may carry 1 or 2 radicals selected from halogen, $C_1$-$C_4$-alkyl, $C_1$-$C_4$-fluoroalkyl, $C_1$-$C_4$-alkoxy and $C_1$-$C_4$-fluoroalkoxy;

$R^1$ is attached to a carbon atom of Het$^2$ and selected from the group consisting of halogen, CN, $NR^{13}R^{14}$, C(O)$NR^{13}R^{14}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $C_1$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^{1a}$ is selected from the group consisting of hydrogen, C(O)$NR^{13}R^{14}$, $C_1$-$C_6$-alkyl, $C_2$-$C_6$-alkenyl, $C_2$-$C_6$-alkynyl, trimethylsilyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^2$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-CO$_2$H, $NR^{23}R^{24}$, C(O)$NR^{23}R^{24}$, $C_1$-$C_4$-alkyl-$NR^{23}R^{24}$, —$NR^{25}$—C(O)—$NR^{23}R^{24}$, $NR^{25}$—C(O)O—($C_1$-$C_4$-alkyl), —$NR^{25}$—SO$_2$—$R^{22}$, phenyl, CN, —SF$_5$, —OSF$_5$, —SO$_2R^{22}$, —$SR^{22}$, trimethylsilyl and $C_3$-$C_6$-cycloalkyl, where the cycloalkyl moiety in the last radical is unsubstituted, partially or completely fluorinated, or substituted by 1, 2 or 3 methyl groups, or two radicals $R^2$, which are bound to adjacent ring atoms may also form linear $C_3$-$C_5$-alkanediyl, wherein 1 or 2 CH$_2$ moieties can be replaced by C=O, O, S, S(=O), S(=O)$_2$ or NR', and where alkanediyl is unsubstituted or may carry 1 or 2 radicals selected from halogen, $C_1$-$C_4$-alkyl, $C_1$-$C_4$-fluoroalkyl, $C_1$-$C_4$-alkoxy and $C_1$-$C_4$-fluoroalkoxy;

$R^{2a}$ has one of the meanings given for $R^2$ or one radical $R^{2a}$ may also be a 5- or 6-membered hetaryl having 1 or 2 nitrogen atoms and optionally a further heteroatom selected from O, S and N as ring members, where hetaryl is unsubstituted or may carry 1, 2 or 3 radicals selected from halogen, OH, $C_1$-$C_4$-alkyl, $C_1$-$C_4$-haloalkyl, $C_1$-$C_4$-alkoxy and $C_1$-$C_4$-haloalkoxy;

$R^{2b}$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-CO$_2$H, $NR^{23}R^{24}$, C(O)$NR^{23}R^{24}$, $C_1$-$C_4$-alkyl-$NR^{23}R^{24}$, —$NR^{25}$—C(O)—$NR^{23}R^{24}$, $NR^{25}$—C(O)O—($C_1$-$C_4$-alkyl), —$NR^{25}$—SO$_2$—$R^{22}$, phenyl, CN, —SF$_5$, —OSF$_5$, —SO$_2R^{22}$, —$SR^{22}$ and trimethylsilyl, or two radicals $R^{2a}$, which are bound to adjacent ring atoms may also form a fused benzene ring or a fused 5- or 6-membered heteroaromatic ring, having 1 ring member selected from the group consisting of O, S, N or NR' and optionally 1 or 2 further N-atoms as ring members, where the fused benzene or heteroaromatic ring is unsubstituted or may carry 1, 2, 3 or 4 radicals selected from halogen, OH, $C_1$-$C_4$-alkyl, $C_1$-$C_4$-fluoroalkyl, $C_1$-$C_4$-alkoxy and $C_1$-$C_4$-fluoroalkoxy;

$R^3$ independently of each other, are selected from the group consisting of halogen, CN, $NR^{33}R^{34}$, C(O)$NR^{33}R^{34}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{31}$, $C_1$-$C_4$-alkyl-$SR^{32}$, $C_1$-$C_4$-alkyl-$NR^{33}R^{34}$, $C_1$-$C_6$-alkoxy, $OC_1$-$C_4$-alkyl-$OR^{31}$, $OC_1$-$C4$-alkyl-$SR^{32}$, $OC_1$-$C_4$-alkyl-$NR^{33}R^{34}$, $C_2$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^{11}$, $R^{12}$ independently of each other are selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl, where $R^{11}$ may also be $C_1$-$C_4$-alkylsulfonyl and $C_1$-$C_4$-fluoroalkylsulfonyl;

$R^{13}$, $R^{14}$ independently of each other are selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl; or $R^{13}$ and $R^{14}$ together with the N atom to which they are attached form a 3- to 7-membered, nitrogen heterocycle which may have 1, 2 or 3 further different or identical heteroatoms or heteroatom containing groups selected from the group of O, N, S, SO and $SO_2$ as ring members and which may carry 1, 2, 3, 4, 5 or 6 substituents selected from $C_1$-$C_4$-alkyl and fluorine;

$R^{21}$, $R^{22}$, $R^{31}$ and $R^{32}$ have one of the meanings given for $R^{11}$, $R^{12}$;

$R^{23}$, $R^{24}$, $R^{33}$ and $R^{34}$ have one of the meanings given for $R^{13}$, $R^{14}$;

$R^{25}$ is selected from the group consisting hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl; and R' is hydrogen, hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl.

The present invention therefore relates to the compounds of the general formula I, the N-oxides, the tautomers, and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I. The present invention in particular relates to the compounds of the general formula I and to their pharmaceutically acceptable salts.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of a medical disorder, selected from neurological and psychiatric disorders which can be treated by modulation of phosphodiesterase type 10.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates effectively inhibit PDE10A even at low concentrations. They are additionally distinguished by a high selectivity in relation to the inhibition of the PDE10A vis-à-vis inhibition of other phosphodiesterase, such as PDE2, PDE3 or PDE4. The compounds of the invention may additionally have one or more of the above mentioned properties ii. to viii.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates are therefore particularly suitable for treating disorders and conditions in creatures, especially human creatures, which can be treated or controlled by inhibition of phosphodiesterase type 10A.

The invention therefore also relates to the use of the compounds of the formula I, their N-oxides, their tautomers, their hydrates and their pharmaceutically acceptable salts and the pharmaceutically acceptable salts of said N-oxides, prodrugs, tautomers or hydrates for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or an N-oxide, a tautomer, or a hydrate or a prodrug of said compound I, or a pharmaceutically acceptable salt of the compound of the formula I or a pharmaceutically acceptable salt of the N-oxide, the tautomer, the hydrate or the prodrug of compound of the formula I.

The invention also relates to a compound of the formula I, in particular of the formulae I-A, I-B, I-A.a, I-B.a, I-A.a' or I-B.a' having an isotope label, in particular a positron emitting isotope label, especially a $^{11}$C-label or a $^{18}$F-label, or a gamma ray emitting isotope label, in particular $^{123}$I. This compounds are valuable diagnostic tools and can be used e.g. in positron emission tomography (PET) and in single photon emission computed tomography (sPECT), respectively.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl(pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH- or $NH_2$-group in which one of the hydrogen atoms of the OH- or $NH_2$-group has been replaced by a group of the formula —C(=O)—O—CHR$^p$—O—C(=O)—R$^q$ in which R$^p$ and R$^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug, tautomer, hydrate or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug, tautomer, hydrate or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). It is preferred to employ the compounds enantiomerically pure or diastereomerically pure.

The present invention moreover relates to compounds as defined herein, wherein one or more of the atoms depicted in formula I have been replaced by a stable isotope (e.g., hydrogen by deuterium, $^{12}C$ by $^{13}C$, $^{14}N$ by $^{15}N$, $^{16}O$ by $^{18}O$) or by an instable, i.e. radioactive isotope (e.g. $^{12}C$ by $^{11}C$, $^{16}O$ by $^{15}O$, $^{19}F$, by $^{18}F$), preferably by a stable, isotope, or enriched with regard to said isotope beyond the natural level. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkynyl", "alkoxy", "fluoroalkyl", "fluoroalkoxy", "cycloalkyl", "fluorinated cycloalkyl", "alkanediyl", "heterocyclyl", "hetaryl", "aryl" and radicals derived therefrom, such as "hydroxylalkyl", "alkoxyalkyl", "alkoxyalkoxy", "alkylsulfanyl", "alkylsulfonyl", "fluorinated alkylsulfanyl", "fluorinated alkylsulfonyl", "cycloalkylalkyl", represent groups of individual radicals. The groups of noncyclic radicals "alkyl", "alkenyl", "alkynyl", "alkoxy", "fluoroalkyl", "fluoroalkoxy", "alkylene", "alkanediyl", and the groups of radicals derived therefrom always include both unbranched and branched "alkyl", "alkenyl", "alkynyl", "alkoxy", "fluoroalkyl", "fluoroalkoxy", "alkylene" and "alkanediyl", respectively.

The prefix $C_n$—$C_m$— indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine.

The term "partially or completely fluorinated" indicates that at least on, e.g. 1, 2, 3, 4, 5 or 6 of the hydrogen atoms or all of the hydrogen atoms of the respective moiety are replaced by halogen atoms, in particular by fluorine atoms Examples of other meanings are:

Alkyl, and the alkyl moieties for example in alkoxy, alkoxyalkyl, alkoxyalkoxy, alkylsulfanyl, alkylsulfonyl: saturated, straight-chain or branched hydrocarbon radicals having one or more C atoms, e.g. 1 to 6 or 1 to 4 carbon atoms. Examples of $C_1$-$C_4$-alkyl are methyl, ethyl, propyl, 1-methylethyl, n-butyl, 1-methylpropyl, 2-methylpropyl and 1,1-dimethylethyl. $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluoroalkyl and the fluoroalkyl moieties for example in fluoroalkyl, fluorinated alkylsulfanyl and fluorinated alkylsulfonyl: an alkyl radical having ordinarily 1 to 6 C atoms, frequently 1 to 4 C atoms, in particular 1 or 2 C-atoms ($C_1$-$C_2$-fluoroalkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy, cycloalkyl-$C_1$-$C_4$-alkyl or cycloalkyl-$C_1$-$C_4$-alkoxy: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl.

Fluorinated cycloalkyl, and the fluorinated cycloalkyl moieties for example in fluorinated cycloalkoxy or fluorinated cycloalkyl-$C_1$-$C_4$-alkyl: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl, wherein at least one, e.g. 1, 2, 3, 4, 5 or 6 or all of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl, cyclohexylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl or 2-cyclohexylethyl.

Fluorinated cycloalkylalkyl: a halogenated, in particular a fluorinated cycloalkyl radical as defined above which is linked via an alkylene group, in particular via a methylene, 1,1-ethylene or 1,2-ethylene group, e.g. 1-fluorocyclopropylmethyl, 2-fluorocyclopropylmethyl, 2,2-difluorocyclopropylmethyl, 1,2-difluorocyclopropylmethyl, 2,3-difluorocyclopropylmethyl, 1-(1-fluorocyclopropyl)ethyl, 1-(2-fluorocyclopropyl)ethyl, 1-(2,2-difluorocyclopropyl)ethyl, 1-(1,2-difluorocyclopropyl)ethyl, 1-(2,3-difluorocyclopropyl)ethyl, 2-(1-fluorocyclopropyl)ethyl, 2-(2-fluorocyclopropyl)ethyl, 2-(2,2-difluorocyclopropyl)ethyl, 2-(1,2-difluorocyclopropyl)ethyl or 2-(2,3-difluorocyclopropyl)ethyl.

Alkenyl: monounsaturated, straight-chain or branched hydrocarbon radicals having two or more C atoms, e.g. 2 to 8, especially 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkynyl: monounsaturated, straight-chain or branched hydrocarbon radicals having two or more C atoms, e.g., e.g. 2 to 8, especially 2 to 6 carbon atoms and one C≡C-triple bond in any position, e.g. $C_2$-$C_4$-alkenyl such as ethynyl, 1-propynyl, 2-propynyl, 1-butynyl, 2-butynyl, 3-butynyl, 1-methyl-2-propynyl, 1-methyl-2-butynyl and 2-methyl-3-butynyl.

Alkoxy or alkoxy moieties for example in alkoxyalkyl and alkoxyalkoxy:

an alkyl radical as defined above having normally 1 to 6 C atoms, in particular 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2-difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

"Alkylsulfanyl": an alkyl radical as defined above having normally 1 to 6 C atoms, in particular 1 to 4 C atoms, which is connected to the remainder of the molecule via an sulfur atom: e.g. methylsulfanyl, ethylsulfanyl, n-propylsulfanyl, 1-methylethsulfanyl, butylsulfanyl, 1-methylpropylsulfanyl, 2-methylpropylsulfanyl or 1,1-dimethylethylsulfanyl.

Fluorinated alkylsulfanyl: alkylsulfanyl as described above, in which the hydrogen atoms of these groups are partly or completely replaced by fluorine atoms, i.e. for example $C_1$-$C_4$-fluoroalkylsulfanyl, in particular $C_1$-$C_2$-fluoroalkylsulfanyl, such as fluoromethylsulfanyl, difluoromethylsulfanyl, trifluoromethylsulfanyl, 2-fluoroethylsulfanyl, 2,2-difluoroethylsulfanyl, 2,2,2-trifluoroethylsulfanyl, pentafluoroethylsulfanyl, 2-fluoropropylsulfanyl, 3-fluoropropylsulfanyl, 2,2-difluoropropylsulfanyl, 2,3-difluoropropylsulfanyl, 3,3,3-trifluoropropylsulfanyl, 2,2,3,3,3-pentafluoropropylsulfanyl, heptafluoropropylsulfanyl, 1-(fluoromethyl)-2-fluoroethylsulfanyl, specifically fluoromethylsulfanyl, difluoromethylsulfanyl, trifluoromethylsulfanyl, 2-fluoroethylsulfanyl, or 2,2,2-trifluoroethylsulfanyl.

"Alkylsulfonyl": an alkyl radical as defined above having normally 1 to 6 C atoms, in particular 1 to 4 C atoms, which is connected to the remainder of the molecule via an $S(O)_2$ moiety: e.g. methylsulfonyl, ethylsulfonyl, n-propylsulfonyl, 1-methylethylsulfonyl, butylsulfonyl, 1-methylpropylsulfonyl, 2-methylpropylsulfonyl or 1,1-dimethylethylsulfonyl.

Fluorinated alkylsulfonyl: alkylsulfonyl as described above, in which the hydrogen atoms of these groups are partly or completely replaced by fluorine atoms, i.e. for example $C_1$-$C_4$-fluoroalkylsulfonyl, in particular $C_1$-$C_2$-fluoroalkylsulfonyl, such as fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, 3,3,3-trifluoropropylsulfonyl, 2,2,3,3,3-pentafluoropropylsulfonyl, heptafluoropropylsulfonyl, 1-(fluoromethyl)-2-fluoroethylsulfonyl, specifically fluoromethylsulfonyl, difluoromethylsulfonyl, trifluoromethylsulfonyl, 2-fluoroethylsulfonyl, or 2,2,2-trifluoroethylsulfonyl.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyethyl, 1-methyl-1-hydroxypropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—OCH (CH₃)₂, n-butoxymethoxy, (1-methylpropoxy)methoxy, (2-methylpropoxy)methoxy, OCH₂—OC(CH₃)₃, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethyl-ethoxy)ethoxy, etc.

"Alkylen" or "Alkanediyl", respectively: a saturated hydrocarbon chain having ordinarily from 1 to 4 carbon atoms, such as methylen (—CH₂—), 1,2-ethylen (—CH₂CH₂—), 1,1-ethandiyl (—CH(CH₃)—), 1,2-propandiyl, 1,3-propandiyl, 1,4-butandiyl, 1,2-butandiyl, 1,3-butandiyl, 1-methyl-1,2-propandiyl, 2-methyl-1,3-propandiyl, 1-methyl-1,1-ethandiyl, 1-methyl-1,2-propandiyl etc.

Saturated or partially unsaturated, heterocyclic radicals include saturated or partially unsaturated, monocyclic heterocyclic radical ordinarily having 3, 4, 5, 6, 7 or 8 ring atoms and heterobicyclic radical ordinarily having 7, 8, 9 or 10 ring atoms. Besides carbon atoms, 1, 2 or 3, of the ring atoms are heteroatoms such as N, S or O, or heteroatom moieties such as NR, S(=O) or S(=O)₂.

Examples of saturated heteromonocyclic radicals are in particular:

Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as: tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as: piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

saturated heterobicyclic radicals which ordinarily have 8, 9 or 10 ring atoms, where ordinarily 1, 2 or 3 of the ring atoms are heteroatoms such as S or O or heteroatom moieties such as NH, N-alkyl, besides carbon atoms as ring members. These include e.g. 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, 2,3,4,4a,5,6,7,7a-octahydro-1H-cyclopenta[b]pyridinyl, 2,3,3a,4,5,6,7,7a-octahydro-1H-indolyl, 1,2,3,4,4a,5,6,7,8,8a-decahydroquinolinyl and 1,2,3,4,4a,5,6,7,8,8a-decahydroisoquinolinyl and the N—C₁-C₄-alkyl analogues;

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as:

2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5- dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as:

2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as:

2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as:

1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-3-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin- 3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

partially unsaturated heterobicyclic radicals, also termed which ordinarily have 8, 9 or 10 ring atoms, where ordinarily 1, 2 or 3 of the ring atoms are heteroatoms such as S or O or heteroatom moieties such as NH, N-alkyl, besides carbon atoms as ring members. These include e.g. 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, 2,3,4,4a,5,6,7,7a-octahydro-1H-cyclopenta[b]pyridinyl, 2,3,3a,4,5,6,7,7a-octahydro-1H-indolyl, 1,2,3,4,4a,5,6,7,8,8a-decahydroquinolinyl and 1,2,3,4,4a,5,6,7,8,8a-decahydroisoquinolinyl and the N—$C_1$-$C_4$-alkyl analogues;

Examples of partially unsaturated heterobicycles are in particular radicals corresponding to saturated or partially unsaturated bicarbocyclic radicals, wherein 1, 2 or 3 CH or $CH_2$ moieties have been replaced by N, NH, O, S, S(=O) or S(=O)$_2$, such as 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, dihydroindolyl, dihydroindolizynyl, dihydroisoindolyl, dihydroquinolinyl, dihydroisoquinolinyl, chromenyl and chromanyl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8-, 9- or 10-membered aromatic heterobicyclic radical (also termed 8-, 9- or 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

bicyclic 8-, 9- 10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizinyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

In relation to their use as inhibitors of PDE10A, the variables $Y^1$, $Y^2$, $Het^1$, k, R, Ar, $Het^2$, Cyc, R, $R^a$, $R^1$, $R^{1a}$, $R^2$, $R^{2a}$, $R^{2b}$, $R^3$, $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ preferably have the following meanings, where these represent, both considered on their own and in combination with at least one other or all, special configurations of the compounds of the formula I:

In a particular preferred group of embodiments both $Y^1$ and $Y^2$ in $Het^1$ are carbon atoms.

In another particular group of embodiments one of $Y^1$ and $Y^2$ in $Het^1$ is a carbon atom while the other of $Y^1$ and $Y^2$ is a nitrogen atom.

In particular, $Het^1$ is a bivalent monocyclic 5-membered heteroaromatic radical, having 1 heteroatom or heteroatom moiety selected from O, S and N—$R^a$ as ring member, and 0, 1 or 2 further nitrogen atoms as ring members.

In a particular group of embodiments, $Het^1$ is a bivalent monocyclic 5-membered heteroaromatic radical, having 1 heteroatom moiety N—$R^a$ and 1 further nitrogen atom as ring members.

In another particular group of embodiments, $Het^1$ is a bivalent monocyclic 5-membered heteroaromatic radical, having 1 heteroatom O or S and 1 further nitrogen atom as ring members.

The variable k indicates the number of substituents R on the carbon atoms of the bivalent radical $Het^1$ and k is in particular 0 or 1, especially 0.

$Het^1$ is in particular selected from the group consisting of 1-($R^a$)-1H-pyrazole-3,4-diyl, 1-($R^a$)-1H-pyrazole-4,5-diyl, 1H-pyrazole-1,5-diyl, 1-($R^a$)-1H-imidazol-4,5-diyl, isoxazol-4,5-diyl, isoxazol-3,4-diyl, 1-($R^a$)-1H-1,2,3-triazol-4,5-diyl, 1H-oxazol-4,5-diyl, 1H-imidazol-1,2-diyl, 1H-imidazol-1,5-diyl and 1H-1,3,4-triazol-1,2-diyl, where the aforementioned radicals carry k substituents R on the carbon atoms of the bivalent radical $Het^1$ and where k is as defined above and k is in particular 0 or 1, especially 0.

The radical R, if present, is in particular selected from the group consisting of halogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of fluorine, $C_1$-$C_2$-alkyl, $C_1$-$C_2$-alkoxy, $C_1$-$C_2$-fluoroalkyl and $C_1$-$C_2$-fluoroalkoxy.

The radical $R^a$, if present, is in particular selected from the group consisting of hydrogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of hydrogen, $C_1$-$C_4$-alkyl and $C_1$-$C_4$-fluoroalkyl.

The radical R and $R^a$, or two radicals R, if present and bound to adjacent atoms in $Het^1$, may in particular also form a linear form linear $C_3$-$C_5$-alkanediyl.

In a group of embodiments, Het² is selected from i. saturated or partially unsaturated, 5- to 10-membered mono- or heterobicyclic radical, having 1, 2 or 3 heteroatoms or heteroatom moieties selected from O, S, S=O, S(=O)₂, N and N—R$^{1a}$ as ring members, ii. monocyclic 5- or 6-membered hetaryl, having 1, 2 or 3 heteroatoms or heteroatom moieties selected from O, S, N and N—R$^{1a}$ as ring members, iii. bicyclic 8-, 9- or 10-membered hetaryl, having 1, 2 or 3 heteroatoms or heteroatom moieties selected from O, S, N and N—R$^{1a}$ as ring members.

In particular, the moiety formed by Het1 and Het2, hereinafter also termed moiety of the formula Het1/2,

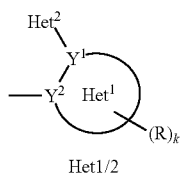

is selected from the following radicals Het1/2a to Het1/2q, in particular from the radicals Het1/2a, Het1/2d, Het1/2g, Het1/2h, Het1/2p and Het1/2q and especially from the radicals Het1/2a and Het1/2q:

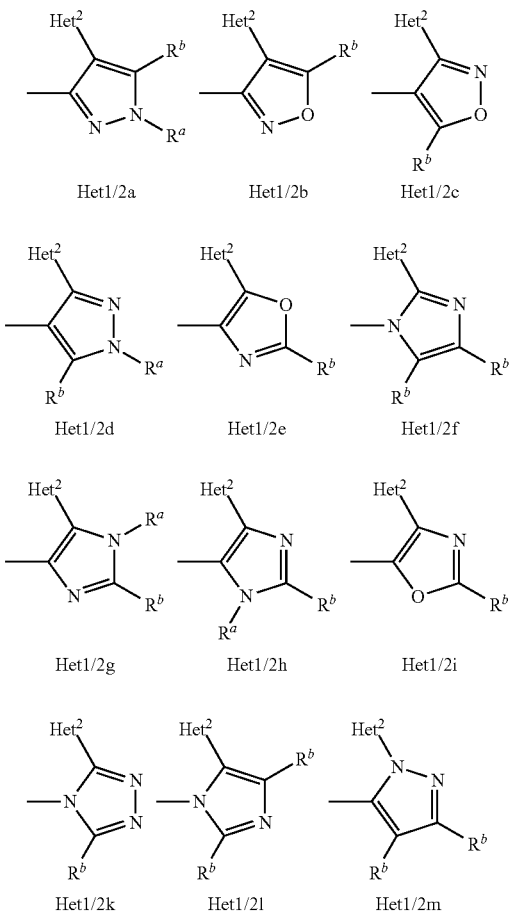

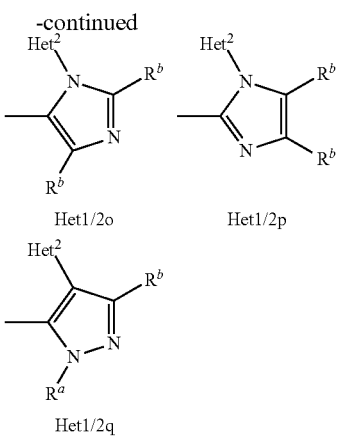

In formulae Het1/2a to Het1/2q the radical R$^a$, if present, is as defined above and the radical R$^b$, if present, is hydrogen or has one of the meanings given above for R. In the groups having two radicals R$^b$, such as Het1/2f, Het1/2l, Het1/2m, Het1/2n, Het1/2o and Het1/2p, the radicals R$^b$ may be identical or different. The radical R$^b$ is in particular selected from the group consisting of hydrogen, halogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of hydrogen, fluorine, $C_1$-$C_2$-alkyl, $C_1$-$C_2$-alkoxy, $C_1$-$C_2$-fluoroalkyl and $C_1$-$C_2$-fluoroalkoxy. Especially R$^b$ is hydrogen.

In formulae Het1/2a to Het1/2q the radical R$^a$, if present, is in particular selected from the group consisting of hydrogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of hydrogen, $C_1$-$C_4$-alkyl and $C_1$-$C_4$-fluoroalkyl.

In formulae Het1/2a, Het1/2d, Het1/2g and Het1/2h, the radical R$^b$ and R$^a$ may in particular also form a linear $C_3$-$C_5$-alkanediyl.

In formulae Het1/2f, Het1/2m, Het1/2n and Het1/2p, the two radical R$^b$ may in particular also form a linear $C_3$-$C_5$-alkanediyl.

Very special embodiments of the invention relate to compounds of the formula I, where the moiety Het1/2 is a moiety of formula Het1/2a, where R$^a$ is as defined above and in particular selected from the group consisting of hydrogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of $C_1$-$C_4$-alkyl and $C_1$-$C_4$-fluoroalkyl and R$^b$ is as defined above and in particular selected from the group consisting of hydrogen, halogen, $C_1$-$C_4$-alkyl, $C_1$-$C_4$-alkoxy, $C_1$-$C_4$-fluoroalkyl and $C_1$-$C_4$-fluoroalkoxy, more particularly from the group consisting of hydrogen, fluorine, $C_1$-$C_2$-alkyl, $C_1$-$C_2$-alkoxy, $C_1$-$C_2$-fluoroalkyl and $C_1$-$C_2$-fluoroalkoxy. Especially R$^b$ in formula Het1/2a is hydrogen.

Further very special embodiments of the invention relate to compounds of the formula I, where the moiety Het1/2 is a moiety of formula Het1/2q, where R$^a$ is as defined above and in particular selected from the group consisting of hydrogen, $C_1$-$C_4$-alkyl, $C_1$-$C_4$-alkoxy, $C_1$-$C_4$-fluoroalkyl and $C_1$-$C_4$-fluoroalkoxy, especially from the group consisting of $C_1$-$C_4$-alkyl and $C_1$-$C_4$-fluoroalkyl and R$^b$ is as defined above and in particular selected from the group consisting of hydrogen, halogen, $C_1$-$C_4$-alkyl, $C_1$-$C_4$-alkoxy, $C_1$-$C_4$-fluoroalkyl and $C_1$-$C_4$-fluoroalkoxy, more particularly from the group consisting of hydrogen, fluorine, $C_1$-$C_2$-alkyl, $C_1$-$C_2$-alkoxy, $C_1$-$C_2$-fluoroalkyl and $C_1$-$C_2$-fluoroalkoxy. Especially R$^b$ in formula Het1/2q is hydrogen.

Particular embodiments of the invention relate to compounds of formula I, where Ar is a radical of the following formula Ar-1:

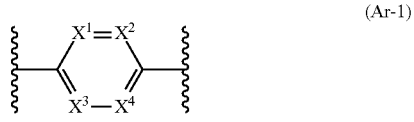
(Ar-1)

where
$X^1$ is N or C—$R^{x1}$;
$X^2$ is N or C—$R^{x2}$;
$X^3$ is N or C—$R^{x3}$;
$X^4$ is N or C—$R^{x4}$;
provided that 0, 1 or 2 of $X^1$, $X^2$, $X^3$ and $X^4$ are N;
and where $R^{x1}$, $R^{x2}$, $R^{x3}$, $R^{x4}$, independently of each other, are hydrogen or have one of the meanings given for $R^3$.
$R^3$, if present, is in particular selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy and especially from the group consisting of fluorine, $C_1$-$C_2$-alkyl, $C_1$-$C_2$-fluoroalkyl, $C_1$-$C_2$-alkoxy and $C_1$-C2-fluoroalkoxy. Hence, $R^{x1}$, $R^{x2}$, $R^{x3}$, $R^{x4}$, independently of each other, are in particular selected from the group consisting of hydrogen, halogen, $C_1$-$C_4$-alkyl, $C_1$-$C_4$-fluoroalkyl, $C_1$-$C_4$-alkoxy and $C_1$-$C_4$-fluoroalkoxy and especially from the group consisting of hydrogen, fluorine, $C_1$-$C_2$-alkyl, $C_1$-$C_2$-fluoroalkyl, $C_1$-$C_2$-alkoxy and $C_1$-$C_2$-fluoroalkoxy. In particular at least 2 of the radicals $R^{x1}$, $R^{x2}$, $R^{x3}$, $R^{x4}$ are hydrogen and especially at least 3 or all of the radicals $R^{x1}$, $R^{x2}$, $R^{x3}$, $R^{x4}$ are hydrogen.

A more particular group of embodiments relates to compounds of the formula I, where Ar is a radical Ar-1, wherein $X^1$ is C—$R^{x1}$, $X^2$ is C—$R^{x2}$, $X^3$ is C—$R^{x3}$ and $X^4$ is C—$R^{x4}$. An even more particular group of embodiments relates to compounds of the formula I, where Ar is a radical Ar-1, wherein $X^1$ is C—$R^{x1}$, $X^2$ is C—$R^{x2}$, $X^3$ is C—$R^{x3}$ and $X^4$ is C—$R^{x4}$, where at least 3 of $R^{x1}$, $R^{x2}$, $R^{x3}$, and $R^{x4}$ are hydrogen and at most one of $R^{x1}$, $R^{x2}$, $R^{x3}$, and $R^{x4}$ is a radical $R^3$ as defined above. A special group of embodiments relates to compounds of the formula I, where Ar is a radical Ar-1, wherein each $X^1$, $X^2$, $X^3$ and $X^4$ is CH.

A particular group of embodiments relates to compounds of the formula I, where Ar is a radical Ar-1 and the moiety Het1/2 is a radical Het1/2a, where $R^b$ is hydrogen. These compounds can be described by the following formula I-A

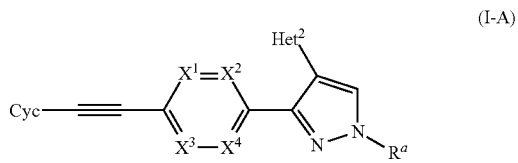
(I-A)

Hence, a particular group of embodiments relates to compounds of the formula I-A, to the N-oxides, the prodrugs, the tautomers and the hydrates thereof, and to the pharmaceutically acceptable salts of the compounds of formula I, the prodrugs, the tautomers and the hydrates thereof, where Cyc, $X^1$, $X^2$, $X^3$, $X^4$, $Het^2$ and $R^a$ are as defined above and where Cyc, $X^1$, $X^2$, $X^3$, $X^4$, $Het^2$ and $R^a$ have in particular the particular or special meanings given above.

Another particular group of embodiments relates to compounds of the formula I, where Ar is a radical Ar-1 and the moiety Het1/2 is a radical Het1/2q, where $R^b$ is hydrogen. These compounds can be described by the following formula I-B

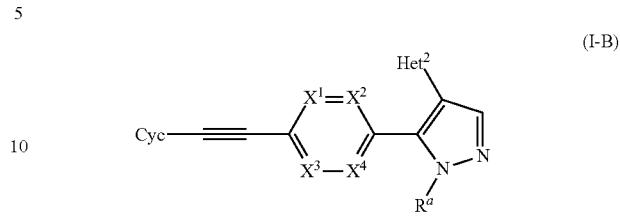
(I-B)

Hence, a particular group of embodiments relates to compounds of the formula I-B, to the N-oxides, the prodrugs, the tautomers and the hydrates thereof, and to the pharmaceutically acceptable salts of the compounds of formula I, the prodrugs, the tautomers and the hydrates thereof, where Cyc, $X^1$, $X^2$, $X^3$, $X^4$, $Het^2$ and $R^a$ are as defined above and where Cyc, $X^1$, $X^2$, $X^3$, $X^4$, $Het^2$ and $R^a$ have in particular the particular or special meanings given above.

In formulae I-A and I-B the variable $X^1$ is in particular C—$R^{x1}$, $X^2$ is in particular C—$R^{x2}$, $X^3$ is in particular C—$R^{x3}$ and $X^4$ is in particular C—$R^{x4}$, where $R^{x1}$, $R^{x2}$, $R^{x3}$, and $R^{x4}$ are as defined above, where in particular at least 3 of $R^{x1}$, $R^{x2}$, $R^{x3}$, and $R^{x4}$ are hydrogen and at most one of $R^{x1}$, $R^{x2}$, $R^{x3}$, and $R^{x4}$ is a radical $R^3$ as defined above.

A special group of embodiments relates to compounds of the formula I-A, wherein each $X^1$, $X^2$, $X^3$ and $X^4$ is CH. These compounds can be described by the following formula I-A.a

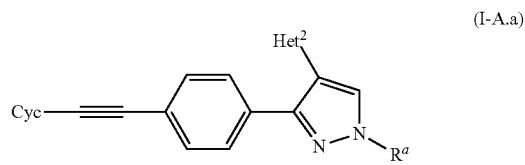
(I-A.a)

Hence, a special group of embodiments relates to compounds of the formula I-A.a, to the N-oxides, the prodrugs, the tautomers and the hydrates thereof, and to the pharmaceutically acceptable salts of the compounds of formula I, the prodrugs, the tautomers and the hydrates thereof, where Cyc, $Het^2$ and $R^a$ are as defined above and where Cyc, $Het^2$ and $R^a$ have in particular the particular or special meanings given above.

Another special group of embodiments relates to compounds of the formula I-B, wherein each $X^1$, $X^2$, $X^3$ and $X^4$ is CH. These compounds can be described by the following formula I-B.a

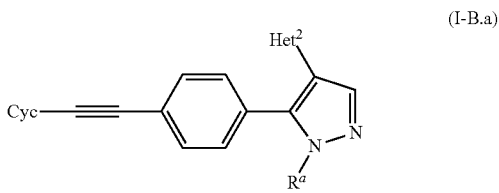
(I-B.a)

Hence, another special group of embodiments relates to compounds of the formula I-B.a, to the N-oxides, the prodrugs, the tautomers and the hydrates thereof, and to the pharmaceutically acceptable salts of the compounds of formula I, the prodrugs, the tautomers and the hydrates thereof, where Cyc, Het² and R^a are as defined above and where Cyc, Het² and R^a have in particular the particular or special meanings given above.

In formulae I, I-A, I-B, I-A a and I-B.a Het² is in particular phenyl or 5- or 6-membered monocyclic hetaryl, which has one heteroatom, selected from O, S and N as ring member and optionally one or two further heteroatoms as ring members, where phenyl and the 5- or 6 membered hetaryl are unsubstituted or carry, independently of each other, 1, 2 or 3, radicals R¹. Het² is more particularly selected from the group consisting of phenyl, oxazolyl, isoxazolyl, furyl, thienyl, pyrrolyl, imidazolyl, pyrazolyl, pyridyl, pyrimidinyl and pyridazinyl, where the aforementioned radicals are unsubstituted or may carry 1, 2 or 3 radicals R¹ as defined above. Even more particularly, the variable Het² in formulae I-A and I-A a is selected from the group consisting of 4-pyrazolyl, 3-pyrazolyl, 4-pyridyl, 4-pyrimidinyl, 5-pyrimidinyl and 4-pyridazinyl where the aforementioned radicals are unsubstituted or may carry 1 or 2 radicals R¹ as defined above.

In particular embodiments of the compounds of formulae I, I-A, I-B, I-A a and I-B.a Het² is 6-membered hetaryl, such as pyridyl, pyrimidinyl or pyridazinyl, which is unsubstituted.

In further particular embodiments of the compounds of formulae I, I-A, I-B, I-A a and I-B.a Het² is phenyl which is substituted by 1 radical R¹, where R¹ is as defined above and in particular selected from the group consisting of halogen, CN, NH₂, NH—C₁-C₂-alkyl, N(C₁-C₂-alkyl)₂, C₁-C₂-alkyl, C₁-C₂-alkoxy, C₁-C₂-fluoroalkyl and C₁-C₂-fluoroalkoxy and especially from the group consisting of fluorine, chlorine, CN, methyl, difluoromethyl, trifluoromethyl, methoxy, difluoromethoxy, trifluoromethoxy and NH₂.

In further particular embodiments of the compounds of formulae I, I-A, I-B, I-A a and I-B.a Het² is 6-membered hetaryl, such as pyridyl, pyrimidinyl or pyridazinyl, which is unsubstituted.

In a special group of embodiments of the compounds of formulae I, I-A, I-B, I-A.a and I-B.a Het² is 4-pyridyl.

A very special group of embodiments relates to compounds of the formula I-A, wherein each X¹, X², X³ and X⁴ is CH and where Het² is 4-pyridyl. These compounds can be described by the following formula I-A.a'

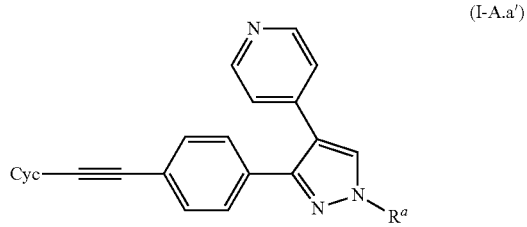

(I-A.a')

Hence, a very special group of embodiments relates to compounds of the formula I-A.a', to the N-oxides, the prodrugs, the tautomers and the hydrates thereof, and to the pharmaceutically acceptable salts of the compounds of formula I, the prodrugs, the tautomers and the hydrates thereof, where Cyc and R^a are as defined above and where Cyc and R^a have in particular the particular or special meanings given above and below.

Another very special group of embodiments relates to compounds of the formula I-B, wherein each X¹, X², X³ and X⁴ is CH and where Het² is 4-pyridyl. These compounds can be described by the following formula I-B.a'

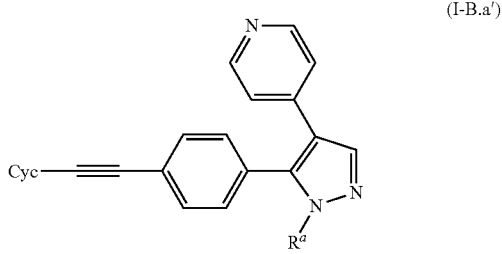

(I-B.a')

Hence, a very special group of embodiments relates to compounds of the formula I-B.a', to the N-oxides, the prodrugs, the tautomers and the hydrates thereof, and to the pharmaceutically acceptable salts of the compounds of formula I, the prodrugs, the tautomers and the hydrates thereof, where Cyc and R^a are as defined above and where Cyc and R^a have in particular the particular or special meanings given above and below.

In formulae I, I-A, I-B, I-A.a, I-B.a, I-A.a' and I-B.a' the radical Cyc is in particular selected from the group consisting of C-bound 5- or 6-membered monocyclic hetaryl, which has 1 or 2 nitrogen atoms as ring members, benzofuryl and C-bound, 9- or 10-membered fused bicyclic hetaryl, which has 1 or 2 nitrogen atoms as ring members and optionally a further heteroatom selected from O, S and N as ring member, where monocyclic hetaryl, benzofuryl and bicyclic hetaryl may be unsubstituted or may carry 1, 2, 3 or 4 substituents R². More particularly, Cyc is selected from the group consisting of C-bound 5- or 6-membered monocyclic hetaryl, which has 1 or 2 nitrogen atoms as ring members, and C-bound, fused 9- or 10-membered bicyclic hetaryl, which has 1 or 2 nitrogen atoms as ring members, monocyclic hetaryl and bicyclic hetaryl may be unsubstituted or may carry 1, 2, 3 or 4 substituents R². In particular Cyc is unsubstituted or carries 1 or 2 substitutents R².

The radical Cyc in formulae I, I-A, I-B, I-A.a, I-B.a, I-A.a' and I-B.a' in particular has at least one imino-nitrogen as ring member, which is located in the position adjacent to the carbon atom which is bound to the triple bond. More particularly, Cyc has at least one imino-nitrogen as ring member, which is located in the position adjacent to the carbon atom which is bound to the triple bond and is selected from the group consisting of C-bound 5- or 6-membered monocyclic hetaryl, which has 1 or 2 nitrogen atoms as ring members, and C-bound, fused 9- or 10-membered bicyclic hetaryl, which has 1 or 2 nitrogen atoms as ring members, monocyclic hetaryl and bicyclic hetaryl may be unsubstituted or may carry 1, 2, 3 or 4 substituents R². In particular Cyc is unsubstituted or carries 1 or 2 substitutents R².

In this context, R², if present, is in particular selected from halogen, C₁-C₄-alkyl, C₁-C₂-fluoroalkyl, C₁-C₄-alkoxy, C₁-C₂-fluoroalkoxy, C₃-C₆-cycloalkyl, and fluorinated C₃-C₆-cycloalkyl. In this regard, R² is especially selected from fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Especially, the radical Cyc in formulae I, I-A, I-B, I-A.a, I-B.a, I-A.a' and I-B.a' is selected from the group consisting of 2-pyridyl, 2-pyrimidinyl, 4-pyrimidinyl, 2-pyrazinyl, 3-pyridazinyl, 2-imidazolyl, 4-imidazolyl, 3-pyrazolyl, 2-thiazolyl, 4-thiazolyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, pyrrolo[2,3-b]pyridine-6-yl, thieno[3,2-b]pyridine-5-yl, imidazo-[2,1-b]-thiazol-6-yl and 1,2,4-triazolo[1,5-a]pyridine-2-yl, where the aforementioned radicals may carry 1, 2 or 3 radicals $R^2$ which are as defined above, and in particular selected from the group consisting of halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl and fluorinated $C_3$-$C_6$-cycloalkyl and especially selected from the group consisting of selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Apart from that, the variables R', $R^{11}$, $R^{12}$, $R^{13}$, $R^{14}$, $R^{21}$, $R^{22}$, $R^{23}$, $R^{24}$, $R^{25}$, $R^{31}$, $R^{32}$, $R^{33}$ and $R^{34}$ particularly have, irrespectively of their occurrence and with regard to the formulae I, I-A, I-B, I-A.a, I-B.a, I-A.a' and I-B.a' and with regard to each of the above mentioned embodiments, groups of embodiments and particularly preferred embodiments one of the following meanings:

$R^{11}$, $R^{21}$, $R^{31}$, independently of each other, are in particular hydrogen, $C_1$-$C_2$-alkyl, $C_1$-$C_2$-fluoroalkyl, methyl, ethyl, difluoromethyl, trifluoromethyl, cyclopropyl, cyclobutyl or cyclopropylmethyl.

$R^{12}$, $R^{22}$, $R^{32}$, $R^{32}$, independently of each other, are in particular $C_1$-$C_4$-alkyl or $C_1$-$C_4$-fluoroalkyl, especially methyl, ethyl, difluoromethyl or trifluoromethyl.

$R^{13}$, $R^{23}$, $R^{33}$, independently of each other, are in particular hydrogen or $C_1$-$C_4$-alkyl, especially hydrogen, methyl, ethyl, propyl or isopropyl.

$R^{14}$, $R^{24}$, $R^{34}$, independently of each other, are in particular hydrogen or $C_1$-$C_4$-alkyl, especially hydrogen, methyl, ethyl, propyl or isopropyl.

$R^{13}$ and $R^{14}$, $R^{23}$ and $R^{24}$, $R^{33}$ and $R^{34}$, respectively, together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl and fluorine.

$R^{25}$ is in particular hydrogen or $C_1$-$C_4$-alkyl, especially hydrogen, methyl, ethyl or propyl or isopropyl.

R' is in particular hydrogen or $C_1$-$C_4$-alkyl, especially hydrogen, methyl, ethyl or propyl or isopropyl.

Particular embodiments of the invention relates to the compounds of formula I, to the N-oxides, the prodrugs, the hydrates and the tautomers thereof and to the pharmaceutically suitable salts thereof, where the compounds of the formula I are selected from the group consisting of:

4-(1-methyl-3-(4-((1-methyl-1H-imidazol-5-yl)ethynyl)phenyl)-1H-pyrazole-4-yl)pyridine,
2-((4-(1-methyl-4-(pyridin-4-yl)-1H-pyrazol-3-yl)phenyl)ethynyl)pyridine,
5-methyl-2-((4-(1-methyl-4-(pyridin-4-yl)-1H-pyrazol-3-yl)phenyl)ethynyl)pyridine,
4-(1-methyl-3-(4-((1-propyl-1H-pyrazol-4-yl)ethynyl)phenyl)-1H-pyrazole-4-yl)pyridine,
5-Fluoro-2-((4-(1-methyl-4-(pyridin-4-yl)-1H-pyrazol-3-yl)phenyl)ethynyl)pyridine,
3-Methyl-2-((4-(1-methyl-4-(pyridin-4-yl)-1H-pyrazol-3-yl)phenyl)ethynyl)pyridine,
4-(1-methyl-3-(4-((1-methyl-1H-imidazol-2-yl)ethynyl)phenyl)-1H-pyrazole-4-yl)pyridine,
4-Methyl-2-((4-(1-methyl-4-(pyridin-4-yl)-1H-pyrazol-3-yl)phenyl)ethynyl)pyridine,
2-Methyl-6-((4-(1-methyl-4-(pyridin-4-yl)-1H-pyrazol-3-yl)phenyl)ethynyl)pyridine,
4-(1-methyl-3-(4-((1-methyl-1H-pyrazol-4-yl)ethynyl)phenyl)-1H-pyrazole-4-yl)pyridine,
4-(3-(4-((1H-pyrazol-4-yl)ethynyl)phenyl)-1-methyl-1H-pyrazole-4-yl)pyridine,
2-((4-(1-methyl-4-(pyridin-4-yl)-1H-pyrazol-3-yl)phenyl)ethynyl)quinoline,
2-[2-[4-[1-methyl-4-(4-pyridyl)pyrazol-3-yl]phenyl]ethynyl]-1,5-naphthyridine,
2-[2-[4-[1-methyl-4-(4-pyridyl)pyrazol-3-yl]phenyl]ethynyl]imidazo[1,2-a]pyridine,
6-[2-[4-[1-methyl-4-(4-pyridyl)pyrazol-3-yl]phenyl]ethynyl]-1H-pyrrolo[2,3-b]pyridine,
4-methyl-2-[2-[4-[1-methyl-4-(4-pyridyl)pyrazol-3-yl]phenyl]ethynyl]quinoline,
2-[2-[4-[1-methyl-4-(4-pyridyl)pyrazol-3-yl]phenyl]ethynyl]thiazole,
2-[2-[4-[1-methyl-4-(4-pyridyl)pyrazol-3-yl]phenyl]ethynyl]quinoxaline,
3-[2-(6-methyl-2-pyridyl)ethynyl]-2-(4-pyridyl)-6,7-dihydro-5H-pyrrolo[1,2-a]imidazole,
2-methoxy-6-[2-[4-[1-methyl-4-(4-pyridyl)pyrazol-3-yl]phenyl]ethynyl]pyridine,
3-methoxy-2-[2-[4-[1-methyl-4-(4-pyridyl)pyrazol-3-yl]phenyl]ethynyl]pyridine,
4-[1-methyl-3-[4-(2-phenylethynyl)phenyl]pyrazol-4-yl]pyridine,
3-[4-[2-(6-methyl-2-pyridyl)ethynyl]phenyl]-2-(4-pyridyl)-6,7-dihydro-5H-pyrrolo[1,2-a]imidazole,
5-[1-methyl-3-[4-[2-(6-methyl-2-pyridyl)ethynyl]phenyl]pyrazol-4-yl]pyrimidine,
2-methyl-6-[2-[4-[1-methyl-4-(1H-pyrazol-4-yl)pyrazol-3-yl]phenyl]ethynyl]pyridine,
2-methyl-6-[2-[4-[2-methyl-4-(4-pyridyl)pyrazol-3-yl]phenyl]ethynyl]pyridine,
2-methyl-6-[2-[4-[1-methyl-4-(2-methylpyrazol-3-yl)pyrazol-3-yl]phenyl]ethynyl]pyridine,
4-[1-methyl-3-[4-[2-(6-methyl-2-pyridyl)ethynyl]phenyl]pyrazol-4-yl]pyridazine,
2-methyl-6-[2-[4-[1-methyl-4-(3-pyridyl)pyrazol-3-yl]phenyl]ethynyl]pyridine,
2-[2-[4-[4-(4-fluorophenyl)-1-methyl-pyrazol-3-yl]phenyl]ethynyl]-6-methylpyridine,
2-[2-[4-[4-(4-methoxyphenyl)-1-methyl-pyrazol-3-yl]phenyl]ethynyl]-6-methylpyridine and 2-[2-[2-methoxy-4-[1-methyl-4-(4-pyridyl)pyrazol-3-yl]phenyl]ethynyl]-6-methylpyridine.

The compounds of the invention of the general formulae I, I-A, I-A.a, I-A.a', I-B, I-B.a and I-B.a' and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

A suitable method for preparing the compounds of the formula I, where $Y^1$ is a carbon atom, comprises the reaction of a compound of the formula II with a compound Het$^2$-M as depicted in scheme 1.

Scheme 1:

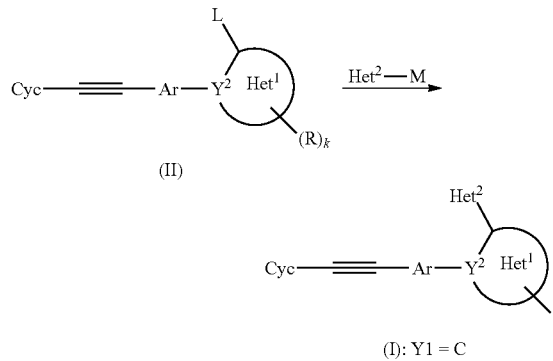

(I): Y1 = C

In scheme 1, the variables k, R, $Y^2$, Ar, Het$^1$, Het$^2$ and Cyc are as defined above. L is a suitable leaving group including halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate. M relates to a metal or metal bound organometal group, such as Li, MgHal, ZnHal, with Hal being Cl, Br or I, a group Sn(R$^{Sn}$)$_3$ wherein R$^{Sn}$ is C$_1$-C$_6$-alkyl or C$_3$-C$_6$-cycloalkyl or phenyl. M may also be B(OR$^{B1}$)(OR$^{B2}$) radical, where R$^{B1}$ and R$^{B2}$ are, independently of each other, hydrogen or C$_1$-C$_4$-alkyl or R$^{B1}$ and R$^{B2}$ together form a C$_2$-C$_6$-alkanediyl moiety, e.g. ethan-1,2-diyl, propan-1,3-diyl or 1,1,2,2-tetramethylethan-1,2-diyl.

The reaction of the compound M-Het$^2$ with the compound of formula II can be performed by analogy to known coupling reactions in the presence of suitable transition metal catalysts, in particular palladium catalysts. Typical reactions conditions are those of Stille coupling and related reactions (see e.g. Stille et al. Angew. Chem. Int. Ed. Engl. 1986, 25, 508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253, T. Zhang et al. Tetrahedron Lett., 52 (2011), 311-313, S. Bourrain et al., Synlett. 5 (2004), 795-798).

A suitable method for preparing the compounds of the formula I, where $Y^1$ is a nitrogen atom, comprises the reaction of a compound of the formula II' with a compound Het$^2$-LG as depicted in scheme 2.

Scheme 2:

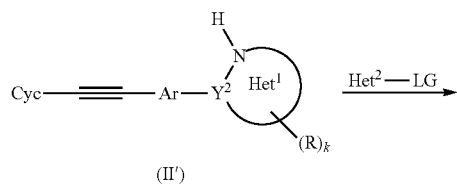

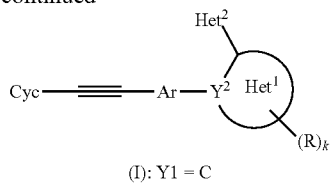

(I): Y1 = C

In scheme 2, the variables k, R, $Y^2$, Ar, Het$^1$, Het$^2$ and Cyc are as defined above. LG is a suitable leaving group including halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate. The reaction of the compound IIa and the compound Het$^2$-LG is usually performed in the presence of a transition metal catalyst such as a palladium catalyst in terms of a Buchwald-Hartwig reaction. Suitable palladium catalysts are for example tris-(dibenzylideneacetone)dipalladium(0) (Pd$_2$(dba)$_3$), [1,1-bis(diphenylphosphino)ferro-cene]dichloro-palladium(II) (PdCl$_2$(dppf)) or palladium acetate (Pd(OAc)$_2$). The reaction is usually carried out in the presence of a tri(substituted)phosphine, e.g. a triaryl-phosphine such as triphenylphosphine, tritolylphosphine or 2,2'-bis(diphenylphosphino)-1,1'-binaphthalene (BINAP), tri (cyclo)alkylphosphine such as tris-n-butylphosphine, tris (tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate. Suitable transition metal catalysts are also copper(I) compounds, e.g. copper(I) iodide. Advantageously the reaction of II' with Het$^2$-LG is then performed in the presence of a diamine ligand. Suitable diamine ligands are 1,10-phenanthroline, trans-N,N'-dimethylcyclohexane-1,2-diamine or trans 1,2-cyclohexanediamine Usually, the reaction is performed in the presence of a base, such as alkaline carbonates such as cesium carbonate or potassium carbonate.

Compounds of the formula I may also prepared by alkyne coupling as depicted in scheme 3:

Scheme 3:

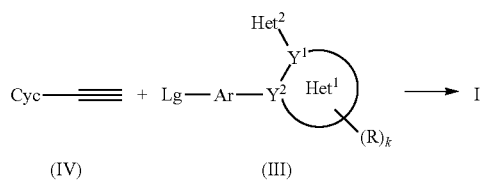

In scheme 3, the variables k, R, $Y^2$, Ar, Het$^1$, Het$^2$ and Cyc are as defined above. Lg is a suitable leaving group including halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate.

The reaction of the compound III with the compound of formula IV can be performed by analogy to known alkyne coupling reactions in the presence of suitable transition metal catalysts, in particular palladium catalysts, e.g. under conditions of a Sonogashira coupling. Typical reactions conditions are described e.g. in Prabakaran, K.; Nawaz Khan F.; Sung Jin J.; Tetahedron Lett. 52 (2011) 2566-2570 or in the examples.

A suitable method for preparing the compounds of the formula I, where $Y^2$ is a carbon atom, comprises the reaction of a compound of the formula V with a compound of formula VI as depicted in scheme 4.

Scheme 4:

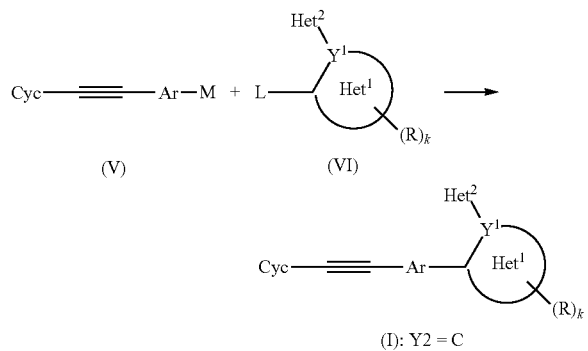

(I): Y2 = C

In scheme 4, the variables k, R, $Y^2$, Ar, $Het^1$, $Het^2$ and Cyc are as defined above. L is a suitable leaving group including halogen such as chlorine, bromine or iodine, alkylsulfonate such as methylsulfonate, phenylsulfonate, alkylphenylsulfonate such as tosylate and perfluoroalkylsulfonate such as triflate, pentaflate, heptaflate or nonaflate. M relates to a metal or metal bound organometal group, such as Li, MgHal, ZnHal, with Hal being Cl, Br or I, a group $Sn(R^{Sn})_3$ wherein $R^{Sn}$ is $C_1$-$C_6$-alkyl or $C_3$-$C_6$-cycloalkyl or phenyl. M may also be $B(OR^{B1})(OR^{B2})$ radical, where $R^{B1}$ and $R^{B2}$ are, independently of each other, hydrogen or $C_1$-$C_4$-alkyl or $R^{B1}$ and $R^{B2}$ together form a C2-C6-alkanediyl moiety, e.g. ethan-1,2-diyl, propan-1,3-diyl or 1,1,2,2-tetramethylethan-1,2-diyl. The reaction conditions are those described for scheme 1.

Compounds of the formulae II, II', III, IV, V and VI are known or may be prepared by analogy to the methods described in the examples hereinafter.

Compounds of the formula II may be prepared by analogy to the method depicted in scheme 3 by reaction of an alkyne of the formula IV with a compound of formula V followed by introduction of the leaving group L, e.g. by halogenation on Het1.

Likewise, compounds of the formula II' may be prepared by analogy to the method depicted in scheme 3 by reaction of an alkyne of the formula IV with a compound of formula V', where Sg is hydrogen or a N-protective group, optionally followed by deprotection.

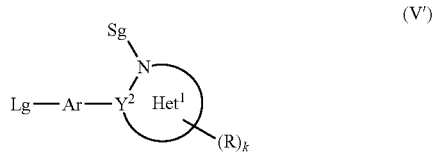

(V')

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from $-10°$ C. to $100°$ C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance use disorders in a mammalian;
a method for treating or ameliorating the symptoms associated with diet-induced obesity in a mammalian;
a method for treating, controlling, ameliorating or reducing the risk of cognitive disturbances associated with Alzheimer's disease in a mammalian;
a method for treating, controlling, ameliorating or reducing the risk of behavioral symptoms in Alzheimer's disease;
a method for treating, controlling, ameliorating or reducing the risk of anxiety in a mammalian;
a method for treating, controlling, ameliorating or reducing the risk of Huntington's disease in a mammalian;
which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-1V.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

Another aspect of the invention relates to the use of the compounds and compositions of the invention, in particular of the compounds of formulae I, I-A, I-B, I-A.a, I-B.a, I-A.a' and I-B.a' as diagnostic tools. The compounds of the invention, which carry a positron-emitting isotope label, in particular $^{11}C$ or $^{18}F$ or another positron-emitting isotope are suitable diagnostic tools for positron emission tomography (PET). The compounds of the invention which carry a gamma ray emitting isotope label, in particular $^{123}I$, are suitable diagnostic tools for single photon emission computed tomography (sPECT).

The ability of PET and sPECT to probe the degree of receptor occupancy in human and animals by endogenous ligands or drugs is widely recognized. This constitutes the use of PET and sPECT as a biomarker to assess efficacy of pharmacological interventions with drugs. The topic and use of positron emitting ligands, i.e. compounds having a positron emitting isotope label, for these purposes has been generally reviewed, for example by Burns et al. in "PET ligands for assessing receptor occupancy in vivo", Annual Reports in Medicinal Chemistry 36 (2001), pp 267-276; Burns et al. "Positron emission tomography neuroreceptor imaging as a tool in drug discovery, research and development" Current Opinion in Chemical Biology 3(4) (1999) 388-394; J. Hietalla "Ligand-receptor interactions as studied by PET: implications for drug development", Annals of Medicine (Helsinki) 31(6) (1999), pp 438-443.

Suitable positions for isotope labels are in particular the radical $R^a$ and the radical $R^3$ in formula I, in particular the compounds of formulae I-A, I-B, I-A.a, I-B.a, I-A.a' and I-B.a'. Suitable labels for pet include $^{11}C$ or $^{18}F$ or another positron-emitting isotope. Suitable labels for sPECT include $^{123}I$. $^{11}C$ may e.g. be present in the form of a $^{11}C$ labeled alkyl group, in particular as $^{11}C$ labeled methyl. $^{18}F$ labels may e.g. be present in the form of $^{18}F$ labeled fluoro-$C_1$-$C_4$-alkyl such as $CH_2CH_2$–$^{18}F$ or as $^{18}F$ which is bound to an aromatic carbon, e.g. as radical $R^3$ bound to Ar. $^{123}I$ may e.g. be present as a label which is bound to an aromatic carbon, e.g. as radical $R^3$ bound to Ar.

The compounds of the invention of formula I, in particular the compounds of formulae I-A, I-B, I-A.a, I-B.a, I-A.a' and I-B.a', which carry a positron-emitting isotope label, in particular a $^{11}C$ or $^{18}F$ or another positron-emitting isotope are suitable ligand tools for PET, in particular PDE10A ligand tools for PET of the brain, especially for PET of the brain of human beings. The compounds of the invention of formula I, in particular the compounds of formulae I-A, I-B, I-A.a, I-B.a, I-A.a' and I-B.a', which carry a gamma ray emitting isotope label, in particular $^{123}I$, are suitable ligand tools for sPECT, in particular PDE10A ligand tools for sPECT of the brain, especially for sPECT of the brain of human beings.

Particular useful compounds of the invention are those, where the isotope label can be incorporated into the compound at a very late stage of the synthesis, e.g. by alkylation with a $^{11}C$ labeled alkylating agent, in particular with a reagent, which is capable of incorporating a $^{11}CH_3$ group such as $^{11}CH_3I$, or by incorporation of a $^{18}F$ label, e.g. by nucleophilic substitution with $^{18}F$ fluoride anions. In this regard, compounds of formulae I-A, I-B, I-A.a, I-B.a, I-A.a' and I-B.a' are particular useful as an isotope labeled radical $R^a$ can be simply incorporated by an alkylation reaction of a precursor of formulae I-A, I-B, I-A.a, I-B.a, I-A.a' and I-B.a', where $R^a$ is hydrogen. It will also be possible to introduce a $^{18}F$ fluorine label by reacting a compound of formula I having a carbon bound leaving group such as bromine, iodine, $C_1$-$C_4$-alkylsulfonyloxy or fluoro-$C_1$-$C_4$-alkylsulfonyloxy, with $^{18}F$ fluoride anions under conditions of a nucleophilic replacement reaction. For example, a compound of formulae I-A, I-B, I-A.a, I-B.a, I-A.a' or I-B.a', where $R^a$ is a radical $C_1$-$C_4$-alkyl-$OR^{11}$, where $R^{11}$ is $C_1$-$C_4$-alkylsulfonyl, e.g. $R^a$ is $CH_2CH_2O$—$SO_2CH_3$, may be reacted with $^{18}F$ fluoride anions under conditions of a nucleophilic replacement reaction to yield a compound where $R^a$ is $^{18}F$ labeled fluoro-$C_1$-$C_4$-alkyl such as $CH_2CH_2$—$^{18}F$. It is likewise possible to introduce an $^{18}F$ label or $^{11}C$-label as a substituent on an aromatic carbon atom, e.g. in the position of $R^3$.

Other useful compounds of the invention are those, where the isotope label can be incorporated into the compound at a very late stage of the synthesis, e.g. by monohalogenation at an aromatic carbon, e.g. by $^{123}I$ replacement of a tri(lower alkyl)tin group, which is bound to an aromatic carbon, e.g. in the position of $R^3$, in the presence of acid and hydrogen peroxide, or by $^{18}F$ replacement of a nitro or trimethylammonium group bound to an aromatic carbon atom such as the $R^3$ group in the presence of [$^{18}F$]KF and kryptofix-2,2,2.

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The following examples are intended for further illustration of the present invention.

EXAMPLES

Abbreviations

MeOH methanol
DCM dichloromethane
DMF dimethylformamide
DMSO dimethyl sulfoxide
THF tetrahydrofuran
TFA trifluoroacetic acid
EtAc ethyl acetate
NBS 1-bromopyrrolidine-2,5-dione
hr hour
HPLC high performance liquid chromatography
MS (ESI) Mass spectrometrie (electron spray ionization)
LC/MS coupled Liquid chromatography-mass spectrometry
prep-HPLC preparative HPLC
RT retention time The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m). Coupling constants are in units of hertz (Hz).

Mass spectra were recorded using electrospray ionization.

Generally, LC-MS was recorded on Agilent 1200 HPLC/ 6110 SQ system. All mass spectra were taken under electrospray ionisation (ESI) methods.

Reverse phase HPLC (TFA method)

Samples were purified by preparative HPLC on a Phenomenex Luna C8(2) 5 um 100 Å AXIA column (30 mm×150 mm) A gradient of acetonitrile (A) and 0.1% trifluoroacetic acid in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A). Samples were injected in 1.5 mL DMSO:MeOH (1:1). An Agilent 1100 Series Purification system was used, consisting of the following modules: Agilent 1100 Series LC/MSD SL mass spectrometer with API-electrospray source; two Agilent 1100 Series preparative pumps; Agilent 1100 Series isocratic pump; Agilent 1100 Series diode array detector with preparative (0.3 mm) flow cell; Agilent active-splitter, IFC-PAL fraction collector/autosampler. The make-up pump for the mass spectrometer used 3:1 methanol:water with 0.1% formic acid at a flow rate of 1 mL/min. Fraction collection was automatically triggered when the extracted ion chromatogram (EIC) for the target mass exceeded the threshold specified in the method. The system was controlled using Agilent Chemstation (Rev B.10.03), Agilent A2Prep, and Leap FractPal software, with custom Chemstation macros for data export.

LC-MS (Method A) was performed by applying the following conditions:

Method Info Mobile Phase: A: Water (0.05% TFA) B: ACN (0.05% TFA)

Gradient: 5% B for 0.1 min, increase to 95% B within 0.7 min, 95% B for 0.9 min, back to 5% B within 0.01 min.

Flow Rate: 3.0 mL/min

Column: Zorbax SB-C18 Rapid Resolution HT, 4.6 mm*30 mm, 1.8 µm

Column Temperature: 45° C.

LC-MS (Method B) was performed by applying the following conditions:

Mobile Phase: A: Water (10 mM $NH_4HCO_3$) B: Acetonitrile

Gradient: 5% B for 0.2 min, increase to 95% B within 1.2 min, 95% B for 1.35 min, back to 5% B within 0.01 min.

Flow Rate: 2 mL/min

Column: XBridge C18, 4.6 mm*50 mm, 3.5 µm

Column Temperature: 50° C.

I. Preparation Examples

PRECURSOR 1: 4-(3-(4-bromophenyl)-1-methyl-1H-pyrazol-4-yl)pyridine 1) (1-(4-bromophenyl)-2-(pyridin-4-yl)ethanone 4-Methylpyridine (10.9 g, 117 mmol) was dissolved in THF (150 ml) and cooled to −78° C. with stirring. Butyllithium (40 ml, 100 mmol) was added slowly to the solution. The resulting solution was stirred at −78° C. for 30 min. A solution of 4-bromobenzonitrile (21.84 g, 120 mmol) in THF (150 ml) was added slowly and the reaction mixture was stirred for 2 h at −78° C. The resulting solution was allowed to warm and it was stirred at 22° C. for 18 h. Water was added, and then acidified with 48% hydrobromic acid. The solvent was removed on the rotary evaporator and the resulting acidic aqueous solution was refluxed for 2 h. The cooled aqueous solution was extracted several times with diethyl ether, and upon neutralization of the acidic aqueous layer, the 4-phenacylpyridine precipitated as a yellow solid (1-(4-bromophenyl)-2-(pyridin-4-yl)ethanone (20 g, 72.4 mmol, 72.4% yield)).

LC-MS (Method B): m/z 278 (M+H), RT: 1.86 min.

2) (E)-1-(4-bromophenyl)-3-(dimethylamino)-2-(pyridin-4-yl)prop-2-en-1-one

A mixture of 1-(4-bromophenyl)-2-(pyridin-4-yl)ethanone (500 mg, 1.811 mmol) and 1,1-dimethoxy-N,N-dimethylmethanamine (1 g, 8.39 mmol) in DMF (9 ml) was heated to 100° C. for about 6 h. Removal of the solvent under reduced pressure provided (E)-1-(4-bromophenyl)-3-(dimethylamino)-2-(pyridin-4-yl)prop-2-en-1-one (640 mg, 1.546 mmol, 85% yield) as a red oil which was used in the next step without further purification.

LC-MS (Method B): m/z 331 (M+H), RT: 1.37 min.

3) 4-(3-(4-bromophenyl)-1-methyl-1H-pyrazol-4-yl)pyridine

A mixture of methylhydrazine (16.59 g, 144 mmol) and (E)-1-(4-bromophenyl)-3-(dimethylamino)-2-(pyridin-4-yl)prop-2-en-1-one (23.85 g, 72 mmol) in MeOH (260 ml) was stirred at about 90° C. for about 5 h. The solution was concentrated to dryness. The crude material was purified by silica gel column eluting with 2% MeOH/DCM to give 4-(3-(4-bromophenyl)-1-methyl-1H-pyrazol-4-yl)pyridine (9.6 g, 30.6 mmol, 42.4% yield).

LC-MS (Method B): m/z 314 (M+H), RT: 1.46 min.

$^1$H NMR (400 mHz, $CDCl_3$): δ 8.51-8.50 (m, 1H), 7.59 (s, 2H), 7.49-7.47 (m, 2H), 7.36-7.33 (m, 2H), 7.16-7.15 (m, 2H), 3.99 (s, 3H).

PRECURSOR 2: 2-[2-[4-(4-bromo-1-methyl-pyrazol-3-yl)phenyl]ethynyl]-6-methylpyridine (1) 3-(4-bromophenyl)-1H-pyrazole 5 g (25.0 mmol) of 4-bromoacetophenone and 3.59 g (30.1 mmol) of 1,1-dimethoxy-N,N-dimethylmethanamine were added to 40 ml of DMF. The mixture was heated to 80° C. for overnight. After cooling, the mixture was poured to water (150 mL) and extracted with EA (100 mL×3). The combined organic phase was washed with brine, concentrated to give red liquid (6 g). The thus obtained product was redissolved in 50 ml of ethanol and treated with hydrazine monohydrate (3.5 ml, 75 mmol). After the reaction was stirred at 80° C. for 2 h, it was cooled to 23° C. and poured to ice-water. Solid was precipitated out of the solution and filtered, washed with water, and dried to give 3.6 g of compound 3-(4-bromophenyl)-1H-pyrazole as yellow solid (yield: 80%).

$^1$H NMR (400 MHz, $CDCl_3$): δ=7.58-7.62 (m, 3H), 7.49-7.51 (m, 2H), 6.58 (d, J=2.4, 1H).

(2) 3-(4-bromophenyl)-1-methylpyrazole and 5-(4-bromophenyl)-1-methylpyrazole

Sodium hydride (0.43 g, 17.9 mmol) was added slowly to a solution of 3-(4-bromophenyl)-1H-pyrazole (1.0 g, 4.48 mmol) in 50 ml of THF under $N_2$. The mixture was stirred for 1 h, then iodomethane (1.27 g, 8.97 mmol) was added to the suspension. The mixture was stirred at 23 for 2 h. Water (20 mL) was added and extracted with EtAc (50 mL×3). The combined organic phase was washed with brine, dried, concentrated and purified by column chromatography to give 1.0 g of colorless liquid (mixture) (yield: 90%).

LC-MS (Method B): m/z 237 (M+H) RT=1.62 min/2.5 min

(3) trimethyl-[2-(6-methyl-2-pyridyl)ethynyl]silane

To a solution of 2-bromo-6-methylpyridine (3 g, 17.44 mmol) in degassed 50 mL of $Et_3N$ was added ethynyltrimethylsilane (1.88 g, 19.2 mmol), copper(I) iodide (0.33 g, 1.74 mmol) and bis(triphenylphosphine)palladium(II) chloride (1.22 g, 1.74 mmol). The resulting solution was stirred at rt for over night under $N_2$. Then the black solution was added with 30 mL of $H_2O$ and extracted with EtAc (50 mL×3). The combined organic phase was washed with brine, dried, concentrated and purified by silical gel column to give 2.5 g of trimethyl-[2-(6-methyl-2-pyridyl)ethynyl]silane as brown liquid (yield: 74%).

$^1$H NMR (400 MHz, $CDCl_3$): δ=7.51 (t, J=8.0 Hz, 1H), 7.27 (d, J=8.0 Hz, 1H), 7.08 (d, J=7.6 Hz, 1H), 2.54 (s, 3H), 0.26 (s, 9H).

(4) 2-[2-[4-(1-methyl-pyrazol-3-yl)phenyl]ethynyl]-6-methylpyridine and 2-[2-[4-(1-methyl-pyrazol-5-yl)phenyl]ethynyl]-6-methylpyridine The mixture of 3-(4-bromophenyl)-1-methylpyrazole and 5-(4-bromophenyl)-1-methylpyrazole (3.0 g, 15.9 mmol) obtained in step 2, trimethyl-[2-(6-methyl-2-pyridyl)ethynyl]silane (3.76 g, 15.8 mmol) and triethylamine (6.41 g, 63.4 mmol), copper(I) iodide (0.30 g, 1.6 mmol) and bis(triphenylphosphine)palladium(II) chloride (1.11 g, 1.60 mmol) were each added sequentially to 30 mL of DMF. The reaction was heated to 60° C., then the solution of tetra-n-butylammonium fluoride (4.6 g, 17.4 mmol) in THF was added slowly to the suspension. The mixture was added with water, filtered and extracted with EtAc (100 mL×3). The combined organic phase was washed with brine, dried, concentrated and purified by silica gel column to give 1.4 g of a mixture of 2-[2-[4-(1-methyl-pyrazol-3-yl)phenyl]ethynyl]-6-methylpyridine and 2-[2-[4-(1-methyl-pyrazol-5-yl)phenyl]ethynyl]-6-methylpyridine (yield: 32%).

LC-MS (Method B): m/z 274 (M+H) RT=1.71 min/2.5 min

(5) 2-[2-[4-(4-bromo-1-methyl-pyrazol-3-yl)phenyl]ethynyl]-6-methylpyridine and 2-[2-[4-(4-bromo-1-methyl-pyrazol-5-yl)phenyl]ethynyl]-6-methylpyridine NBS (3.94 g, 22.1 mmol) was added to a solution of the mixture obtained in step 4 (5.5 g, 20.1 mmol) in 50 mL of dry DMF. The mixture was stirred at 23° C. for 30 min and then poured into 100 ml of $H_2O$. A white precipitate that formed was extracted with EtAc (150 ml×3). The combined organic phase was washed with brine, dried, concentrated and purified by Prep-HPLC to give 2.0 g of 2-[2-[4-(4-bromo-1-methyl-pyrazol-3-yl)phenyl]ethynyl]-6-methylpyridine and 2.5 g of 2-[2-[4-(4-bromo-1-methyl-pyrazol-5-yl)phenyl]ethynyl]-6-methylpyridine (yield: 63.5%).

2-[2-[4-(4-bromo-1-methyl-pyrazol-3-yl)phenyl]ethynyl]-6-methylpyridine $^1$H NMR (400 MHz, $CDCl_3$): δ=7.91 (d, J=8.4 Hz, 2H), 7.65 (d, J=8.4 Hz, 2H), 7.57 (t, J=8.0 Hz, 1H), 7.46 (s, 1H), 7.36 (d, J=7.6 Hz, 1H), 7.11 (d, J=7.6 Hz, 1H), 3.93 (s, 3H), 2.59 (s, 3H).

Method of Prep-HPLC:

| Main Solvent | MeOH (containing 0.1% DEA) |
|---|---|
| Column | OJ-H 4.6 mm * 250 mm 5 μm (Daicel Chemical Industries Co. Ltd) |
| Sample Well | P1: 2C |
| Column Temperature | 40° C. |
| $CO_2$ Flow Rate | 2.25 |
| Co-Solvent Flow Rate | 0.75 |
| Co-Solvent % | 25 |
| Total Flow | 3 |
| Front Pressure | 196 |
| Back Pressure | 150 |
| Pressure Drop | 46 |
| PDA Start Wavelength | 214 nm |
| PDA Stop Wavelength | 359 nm |

PRECURSOR 3: 2-[2-[4-(4-bromo-1-methyl-pyrazol-5-yl)phenyl]ethynyl]-6-methylpyridine The compound was prepared as described for Precursor 2 and isolated from crude reaction product.

$^1$H NMR (400 MHz, $CDCl_3$): δ=7.72 (d, J=8.0, 2H), 7.59 (t, J=8.0 Hz, 1H), 7.54 (s, 1H), 7.41 (d, J=8.4 Hz, 2H), 7.38 (d, J=7.6 Hz, 1H), 7.14 (d, J=8.0 Hz, 1H), 3.83 (s, 3H), 2.60 (s, 3H).

Precursor 4: 3-Bromo-2-(4-pyridyl)-6,7-dihydro-5H-pyrrolo[1,2-a]imidazole

1) Pyrrolidin-2-imine hydrochloride

In a 250 mL bottomed flask, ammonia was bubbled into ethanol (80 mL) that was cooled to −78° C. for 45 min. The thus obtained saturated solution was transferred to a Parr autoclave, which contained 4-chlorobutanenitrile (60 g, 580 mmol) and the mixture was stirred and heated to 120° C. for 16 hr. The reaction mixture was cooled and transferred to a round-bottomed flask and the solvent was removed under reduced pressure to afford a yellow solid, which was washed with diethyl ether and dried under high vacuum to afford an off-white solid, 19.5 g, 232 mmol, 40% yield.

$^1$H NMR (DMSO-d6) δ 9.22 (br s, 1H), 8.93 (br s, 1H), 7.60 (br s, 1H), 3.52 (d, J=7.2 Hz, 2H), 2.76 (d. J=8.0 Hz, 2H), 2.08-1.96 (m, 2H).

2) 2-(pyridin-4-yl)-6,7-dihydro-5H-pyrrolo[1,2-a]imidazole

A mixture of 2-bromo-1-(pyridin-4-yl)ethanone (12.8 g, 64 mmol), pyrrolidin-2-imine hydrochloride (10.8 g, 89.4 mmol) and $Na_2CO_3$ (33.8 g, 319 mmol) in DMF (65 mL) was stirred and heated to 80° C. in a 250 mL three-necked flask for 16 hrs. The mixture was cooled to 22° C. and poured into water (500 mL). The product was partitioned between ethyl acetate (300 mL) and aqueous phase. The aqueous phase was extracted three time with ethyl acetate (300 mL each). The combined organic phases were washed with water, then brine and dried over anhydrous $Na_2SO_4$. After filtration, the filtrate was concentrated to afford grey solid, 2-(pyridin-4-yl)-6,7-dihydro-5H-pyrrolo[1,2-a]imidazole (7.03 g, 38 mmol), 60% yield.

3) 3-bromo-2-(pyridin-4-yl)-6,7-dihydro-5H-pyrrolo[1,2-a]imidazole

NBS (890 mg, 5 mmol) was added in portions to a stirred solution of 2-(pyridin-4-yl)-6,7-dihydro-5H-pyrrolo[1,2-a]

imidazole (740 mg, 4 mmol) in DMF (10 mL) cooled by means of an ice-water bath to keep the inner temperature between 15 and 20° C. After complete addition, the mixture was stirred at 22° C. for 2 hr. The reaction mixture was poured into ice water and was stirred at 22° C. for 15 min and then a 10% aqueous solution of $Na_2S_2O_3$ was added. The resulting solution was stirred for 1 hr and then it was extracted with ethyl acetate. The combined organic phase was washed with water, followed by brine, dried over anhydrous $Na_2SO_4$. After evaporation under reduced pressure a crude product was obtained which was purified through chromatography column (MeOH/DCM=1/10) to afford an pale yellow solid, 3-bromo-2-(pyridin-4-yl)-6,7-dihydro-5H-pyrrolo[1,2-a]imidazole (924 mg, 3.5 mmol), 87% yield.

LCMS (ESI+): m/z 266 (M+H)$^+$, RT: 1.64 min. (Method A)

Example 1: 4-(1-methyl-3-(4-((1-methyl-1H-imidazol-5-yl)ethynyl)phenyl)-1H-pyrazole-4-yl)pyridine In a 4 mL vial, 2-dicyclohexylphosphino-2',6'-diisopropoxybiphenyl (28 mg, 0.06 mmol) was added, followed by Palladium(II) acetate (5.5 mg, 0.02 mmol) and triethylamine neat (51 µL, 0.37 mmol). To this, 4-(3-(4-bromophenyl)-1-methyl-1H-pyrazol-4-yl)pyridine (38 mg, 0.12 mmol) dissolved in a 10% water/THF solution (1.0 mL) was added, followed by 5-ethynyl-1-methyl-1H-imidazole (358 mg, 0.36) dissolved in a 10% water/THF solution (0.9 mL). This was capped with a septa cap, evacuated and purged with nitrogen 3-4 times. This was placed to stir at 80 degrees Celsius for 5 hours. Upon 5 hours treat again with same amounts of 2-dicyclohexylphosphino-2',6'-diisopropoxybiphenyl, palladium(II)acetate, triethylamine, and 5-ethynyl-1-methyl-1H-imidazole, repurge with nitrogen and placed to stir at 80 degrees Celsius for 16 hr. Upon completion pass product through Celite cartridge. The reaction was checked by LC/MS and dried down. The residues were dissolved in 1:1 DMSO/MeOH. Purification by reverse phase HPLC (TFA method), provided the titled compound (8.9 mg, 13%). Products were characterized by $^1$H NMR, MS and LC/MS.

$^1$H NMR (500 MHz, DMSO-D$_2$O, 27° C.) δ ppm 8.97 (s, 1H) 8.67 (d, J=6.71 Hz, 2H) 8.52 (s, 1H) 8.01 (s, 1H) 7.75 (dd, J=14.19, 7.78 Hz, 4H) 7.57 (d, 2H) 3.99 (s, 3H) 3.90 (s, 3H); MS (ESI) m/z 340 (M+H)$^+$.

The compounds of examples 2 to 11 and 13 to 23 were prepared by analogy to the method depicted in Example 1.

Example 2: 2-((4-(1-methyl-4-(pyridin-4-yl)-1H-pyrazol-3-yl)phenyl)ethynyl)pyridine $^1$H NMR (500 MHz, DMSO-D$_2$O 27° C.) δ ppm 8.69 (d, J=7.02 Hz, 2H) 8.64 (d, J=4.88 Hz, 1H) 8.54 (s, 1H) 7.89-7.95 (m, 1H) 7.81 (d, J=6.71 Hz, 2H) 7.71 (d, J=8.24 Hz, 3H) 7.56 (d, J=8.54 Hz, 2H) 7.45-7.50 (m, 1H) 4.00 (s, 3H);

MS (ESI) m/z 337 (M+H)$^+$.

Example 3: 5-methyl-2-((4-(1-methyl-4-(pyridin-4-yl)-1H-pyrazol-3-yl)phenyl)ethynyl)pyridine $^1$H NMR (500 MHz, DMSO-D$_2$O 27° C.) δ ppm 8.69 (d, J=6.71 Hz, 2H) 8.54 (s, 1H) 8.49 (s, 1H) 7.75-7.84 (m, 3H) 7.70 (d, J=8.24 Hz, 2H) 7.63 (d, J=8.24 Hz, 1H) 7.53-7.59 (m, 2H) 4.00 (s, 3H) 2.37 (s, 3H);

MS (ESI) m/z 351 (M+H)$^+$.

Example 4: 4-(1-methyl-3-(4-((1-propyl-1H-pyrazol-4-yl)ethynyl)phenyl)-1H-pyrazole-4-yl)pyridine $^1$H NMR (500 MHz, DMSO-D$_2$O, 27° C.) δ ppm 8.66 (d, J=6.71 Hz, 2H) 8.51 (s, 1H) 8.11 (s, 1H) 7.71-7.78 (m, 3H) 7.45-7.60 (m, 4H) 4.09 (t, J=7.02 Hz, 2H) 3.98 (s, 3H) 1.74-1.85 (m, 2H) 0.79-0.85 (m, 3H);

MS (ESI) m/z 368 (M+H)$^+$.

Example 5: 5-Fluoro-2-((4-(1-methyl-4-(pyridin-4-yl)-1H-pyrazol-3-yl)phenyl)ethynyl)pyridine $^1$H NMR (500 MHz, DMSO-D$_2$O, 27° C.) δ ppm 8.66 (d, J=6.71 Hz, 2H) 8.63 (d, J=2.75 Hz, 1H) 8.51 (s, 1H) 7.77-7.83 (m, 2H) 7.76 (d, J=7.02 Hz, 2H) 7.69 (d, J=8.54 Hz, 2H) 7.53-7.57 (m, 2H) 3.99 (s, 3H);

MS (ESI) m/z 355 (M+H)$^+$.

Example 6: 3-Methyl-2-((4-(1-methyl-4-(pyridin-4-yl)-1H-pyrazol-3-yl)phenyl)ethynyl)pyridine $^1$H NMR (500 MHz, DMSO-D$_2$O, 27° C.) δ ppm 8.69 (d, J=7.02 Hz, 2H) 8.54 (s, 1H) 8.48 (d, J=4.88 Hz, 1H) 7.87 (d, J=7.02 Hz, 1H) 7.81 (d, J=6.41 Hz, 2H) 7.73 (d, J=8.54 Hz, 2H) 7.58 (d, J=8.54 Hz, 2H) 7.41-7.47 (m, 1H) 4.00 (s, 3H) 2.52 (s, 3H);

MS (ESI) m/z 351 (M+H)$^+$.

Example 7: 4-(1-methyl-3-(4-((1-methyl-1H-imidazol-2-yl)ethynyl)phenyl)-1H-pyrazole-4-yl)pyridine $^1$H NMR (500 MHz, DMSO-D$_2$O, Temp=27° C.) δ ppm 8.68 (d, J=6.71 Hz, 2H) 8.52 (s, 1H) 7.78 (dd, J=12.66, 7.48 Hz, 4H) 7.68 (d, J=1.83 Hz, 1H) 7.62 (d, J=8.54 Hz, 2H) 7.56 (d, J=1.53 Hz, 1H) 4.00 (s, 3H) 3.91 (s, 3H);

MS (ESI) m/z 340 (M+H)$^+$.

Example 8: 4-Methyl-2-((4-(1-methyl-4-(pyridin-4-yl)-1H-pyrazol-3-yl)phenyl)ethynyl)pyridine $^1$H NMR (500 MHz, DMSO-D$_2$O, 27° C.) δ ppm 8.68 (d, J=7.02 Hz, 2H) 8.53 (s, 1H) 8.49 (d, J=5.19 Hz, 1H) 7.79 (d, J=7.02 Hz, 2H) 7.70 (d, 2H) 7.53-7.61 (m, 3H) 7.35 (d, J=6.10 Hz, 1H) 4.00 (s, 3H) 2.39 (s, 3H);

MS (ESI) m/z 351 (M+H)$^+$.

Example 9: 2-Methyl-6-((4-(1-methyl-4-(pyridin-4-yl)-1H-pyrazol-3-yl)phenyl)ethynyl)pyridine $^1$H NMR (500 MHz, DMSO-D$_2$O, Temp=27° C.) δ ppm 8.70 (d, J=6.71 Hz, 2H) 8.55 (s, 1H) 7.97 (t, J=7.93 Hz, 1H) 7.82 (d, J=6.71 Hz, 2H) 7.72-7.75 (m, 2H) 7.64-7.68 (m, 1H) 7.56-7.60 (m, 2H) 7.49 (d, J=7.93 Hz, 1H) 4.00 (s, 3H) 2.58 (s, 3H);

MS (ESI) m/z 351 (M+H)$^+$.

Example 10: 4-(1-methyl-3-(4-((1-methyl-1H-pyrazol-4-yl)ethynyl)phenyl)-1H-pyrazole-4-yl)pyridine $^1$H NMR (500 MHz, DMSO-D$_2$O, 27° C.) δ ppm 8.44-8.48 (m, 2H) 8.15 (s, 1H) 8.05 (s, 1H) 7.69 (s, 1H) 7.47-7.52

(m, 2H) 7.40-7.44 (m, 2H) 7.21-7.27 (m, 2H) 3.94 (s, 3H) 3.86 (s, 3H);
MS (ESI) m/z 340 (M+H)+.

Example 11: 4-(3-(4-((1H-pyrazol-4-yl)ethynyl) phenyl)-1-methyl-1H-pyrazole-4-yl)pyridine $^1$H NMR (500 MHz, DMSO-D$_2$O, Temp=27° C.) δ ppm 8.44-8.48 (m, 2H) 8.15 (s, 1H) 7.93 (s, 2H) 7.47-7.53 (m, 2H) 7.39-7.44 (m, 2H) 7.22-7.28 (m, 2H) 3.94 (s, 3H);
MS (ESI) m/z 326 (M+H)+.

Example 12: 2-((4-(1-methyl-4-(pyridin-4-yl)-1H-pyrazol-3-yl)phenyl)ethynyl)quinoline 4-(3-(4-bromophenyl)-1-methyl-1H-pyrazol-4-yl)pyridine (200 mg, 0.637 mmol) was added to a suspension of tetrakis(triphenylphosphine)palladium(0) (36.8 mg, 0.032 mmol) and Copper(I) Iodide (6.06 mg, 0.032 mmol) in DMF (1 mL). 2-ethynylquinoline (134 mg, 0.700 mmol) in DMF (3 mL) was added followed by addition of triethylamine (0.106 ml, 0.764 mmol). The vessel was flushed with Argon and then the mixture was stirred and heated in the microwave (110° C., 300 W, 2 h). Water and EtOAc were added, the organic layer was separated and the aqueous layer was extracted with EtOAc. The combined organic layers were washed with water and dried over MgSO4. Purification by flash chromatography (DCM/AcCN) provided 2-((4-(1-methyl-4-(pyridin-4-yl)-1H-pyrazol-3-yl)phenyl)ethynyl) quinoline (70 mg, 29%).
ESI-MS [M+H+]=387.1;
$^1$H-NMR (DMSO) δ ppm: 3.93 (s, 3H), 7.25 (d, 2H), 7.50 (d, 2H), 7.70 (m, 2H), 7.73 (d, 1H), 7.78 (t, 1H), 8.02 (d, 2H), 8.20 (s, 1H), 8.46 (d, 1H), 8.50 (d, 2H).

Example 13: 2-[2-[4-[1-methyl-4-(4-pyridyl)pyrazol-3-yl]phenyl]ethynyl]-1,5-naphthyridine MS (ESI) [M+Na+]=410.20, [M+H+]=388.20

Example 14: 2-[2-[4-[1-methyl-4-(4-pyridyl)pyrazol-3-yl]phenyl]ethynyl]imidazo[1,2-a]pyridine

MS (ESI) [M+H+]=376.10

Example 15: 6-[2-[4-[1-methyl-4-(4-pyridyl)pyrazol-3-yl]phenyl]ethynyl]-1H-pyrrolo[2,3-b]pyridine

MS (ESI) [M+H+]=376.10

Example 16: 4-methyl-2-[2-[4-[1-methyl-4-(4-pyridyl)pyrazol-3-yl]phenyl]ethynyl]quinoline

MS (ESI) [M+H+]=401.10

Example 17: 2-[2-[4-[1-methyl-4-(4-pyridyl)pyrazol-3-yl]phenyl]ethynyl]thiazole; 2,2,2-trifluoroacetic acid

MS (ESI) [M+H+]=343.10

Example 18: 2-[2-[4-[1-methyl-4-(4-pyridyl)pyrazol-3-yl]phenyl]ethynyl]quinoxaline; 2,2,2-trifluoroacetic acid

MS (ESI) [M+H+]=388.20

Example 19: 3-[2-(6-methyl-2-pyridyl)ethynyl]-2-(4-pyridyl)-6,7-dihydro-5H-pyrrolo[1,2-a]imidazole; 2,2,2-trifluoroacetic acid

MS (ESI) [M+H+]=301.10

Example 20: 2-methoxy-6-[2-[4-[1-methyl-4-(4-pyridyl)pyrazol-3-yl]phenyl]ethynyl]pyridine; 2,2,2-trifluoroacetic acid MS (ESI) [M+Na+]=389.10, [M+H+]=367.10

Example 21: 3-methoxy-2-[2-[4-[1-methyl-4-(4-pyridyl)pyrazol-3-yl]phenyl]ethynyl]pyridine

MS (ESI) [M+H+]=367.10

Example 22: 4-[1-methyl-3-[4-(2-phenylethynyl) phenyl]pyrazol-4-yl]pyridine; 2,2,2-trifluoroacetic acid

MS (ESI) MS (ESI) [M+H+]=336.90

Example 23: 3-[4-[2-(6-methyl-2-pyridyl)ethynyl] phenyl]-2-(4-pyridyl)-6,7-dihydro-5H-pyrrolo[1,2-a] imidazole

MS (ESI) [M+H+]=377.90

Example 24: 2-methyl-6-[2-[4-[1-methyl-4-(1H-pyrazol-4-yl)pyrazol-3-yl]phenyl]ethynyl]pyridine To 2-((4-(4-bromo-1-methyl-1H-pyrazol-3-yl)phenyl) ethynyl)-6-methylpyridine (25 mg, 0.07 mmol), 4-(4,4,5,5-tetramethyl-1,3,2-dioxaborolan-2-yl)-1H-pyrazole (14 mg, 0.07 mmol) and Pd(PPh$_3$)$_4$ (8.2 mg, 7 μmol) in dioxane (2 ml) was added a saturated aq. NaHCO$_3$ solution (1.5 ml). The mixture was then stirred for 10 min under microwave (CEM device) at 150° C. and 300 W. The mixture was poured onto aq. K$_2$CO$_3$ (5%, 10 ml), extracted with ethyl acetate (3×, 10 ml). The combined organic phases were washed with water (3×, 30 ml), dried on Na$_2$SO$_4$, filtered and evaporated in vacuo. The residue oil was purified on silica gel (preparative TLC, CH$_2$Cl$_2$:MeOH 19:1) to give the title compound (4.4 mg, 18%).
$^1$H NMR (CDCl$_3$, 600 MHz) δ ppm=7.61-7.50 (m, 8H), 7.45 (s, 1H), 7.36 (d, 1H), 7.12 (d, 1H), 3.97 (s, 3H), 2.60 (s, 3H).
The compounds of examples 25 to 32 were prepared by analogy to example 24 using precursors 2 or 3.

Example 25: 5-[1-methyl-3-[4-[2-(6-methyl-2-pyridyl)ethynyl]phenyl]pyrazol-4-yl]pyrimidine MS (ESI) [M+Na+]=374.10, [M+H+]=352.10

Example 26: 2-methyl-6-[2-[4-[2-methyl-4-(4-pyridyl)pyrazol-3-yl]phenyl]ethynyl]pyridine

MS (ESI) [M+H+]=351.10

Example 27: 2-methyl-6-[2-[4-[1-methyl-4-(2-methylpyrazol-3-yl)pyrazol-3-yl]phenyl]ethynyl]-pyridine hydrochloride

MS (ESI) [M+H+]=354.10

Example 28: 4-[1-methyl-3-[4-[2-(6-methyl-2-pyridyl)ethynyl]phenyl]pyrazol-4-yl]pyridazine

MS (ESI) [M+H+]=352.10

Example 29: 2-methyl-6-[2-[4-[1-methyl-4-(3-pyridyl)pyrazol-3-yl]phenyl]ethynyl]pyridine; 2,2,2-trifluoroacetic acid MS (ESI) [M+Na+]=373.10, [M+H+]=351.10

Example 30: 2-[2-[4-[4-(4-fluorophenyl)-1-methyl-pyrazol-3-yl]phenyl]ethynyl]-6-methyl-pyridine; 2,2,2-trifluoroacetic acid

MS (ESI) [M+H+]=368.10

Example 31: 2-[2-[4-[4-(4-methoxyphenyl)-1-methyl-pyrazol-3-yl]phenyl]ethynyl]-6-methylpyridine; 2,2,2-trifluoroacetic acid

MS (ESI) [M+H+]=380.10

Example 32: 2-[2-[2-methoxy-4-[1-methyl-4-(4-pyridyl)pyrazol-3-yl]phenyl]ethynyl]-6-methylpyridine; 2,2,2-trifluoroacetic acid

MS (ESI) [M+H+]=381.10

II. Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM $MgCl_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, $IC_{50}$ value of inhibitor can be obtained by plotting inhibitor concentration against PDE activity at that concentration. The results are shown in Table 1.

TABLE 1

| EXAMPLE | $IC_{50}$ |
|---|---|
| 2 | +++ |
| 3 | +++ |
| 5 | +++ |
| 6 | +++ |
| 7 | +++ |
| 8 | +++ |
| 9 | +++ |
| 12 | +++ |
| 13 | +++ |
| 14 | +++ |
| 15 | +++ |
| 16 | +++ |
| 17 | ++ |
| 18 | +++ |
| 20 | +++ |
| 21 | +++ |
| 23 | ++ |
| 24 | + |
| 25 | ++ |
| 26 | +++ |
| 27 | ++ |
| 28 | +++ |
| 29 | + |
| 31 | ++ |
| 32 | +++ |

1) +++: $IC_{50} < 100$ nM ++: $100$ nM $\leq IC_{50} \leq 200$ nM +: $200$ nM $< IC_{50} < 500$ nM b) Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T1/2) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T1/2/(content of microsomal protein in mg/ml)×1000 [ml/min/mg] (modified from references: Di, The Society for Biomoleculur Screening, 2003, 453-462; Obach, DMD, 1999 vol 27. N 11, 1350-1359). The results are shown in Table 2.

TABLE 2

| Ex. | Rat mCl[2] [µl $min^{-1}$ $mg^{-1}$] | Human mCl[2] [µl $min^{-1}$ $mg^{-1}$] |
|---|---|---|
| 2 | ++ | ++ |
| 3 | ++ | ++ |
| 4 | n.a. | ++ |
| 5 | ++ | ++ |
| 6 | ++ | ++ |
| 7 | ++ | ++ |
| 8 | ++ | ++ |
| 9 | ++ | ++ |
| 12 | ++ | ++ |
| 13 | ++ | ++ |
| 14 | ++ | ++ |
| 15 | ++ | ++ |

TABLE 2-continued

| Ex. | Rat mCl[2] [μl min$^{-1}$ mg$^{-1}$] | Human mCl[2] [μl min$^{-1}$ mg$^{-1}$] |
|---|---|---|
| 16 | ++ | ++ |
| 17 | ++ | ++ |
| 18 | ++ | ++ |
| 19 | + | + |
| 20 | ++ | ++ |
| 21 | ++ | ++ |
| 23 | ++ | ++ |
| 24 | ++ | ++ |
| 26 | ++ | ++ |
| 27 | + | ++ |
| 29 | ++ | ++ |
| 32 | + | ++ |

Ex. EXAMPLE
mCl microsomal clearance
[2] ++: <100 μl min$^{-1}$ mg$^{-1}$ +: 100-220 μl min$^{-1}$ mg$^{-1}$ o: >220 μl min$^{-1}$ mg$^{-1}$ n.a. not available

We claim:

1. A compound of formula (I)

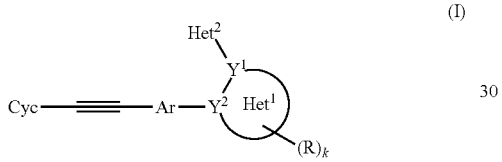

or a pharmaceutically acceptable salt thereof;

where in form (I) the moiety of the formula Het1/2

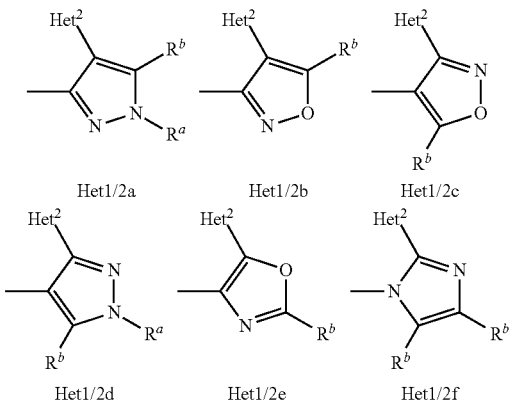

is selected from the following radicals Het1/2a to Het1/2q:

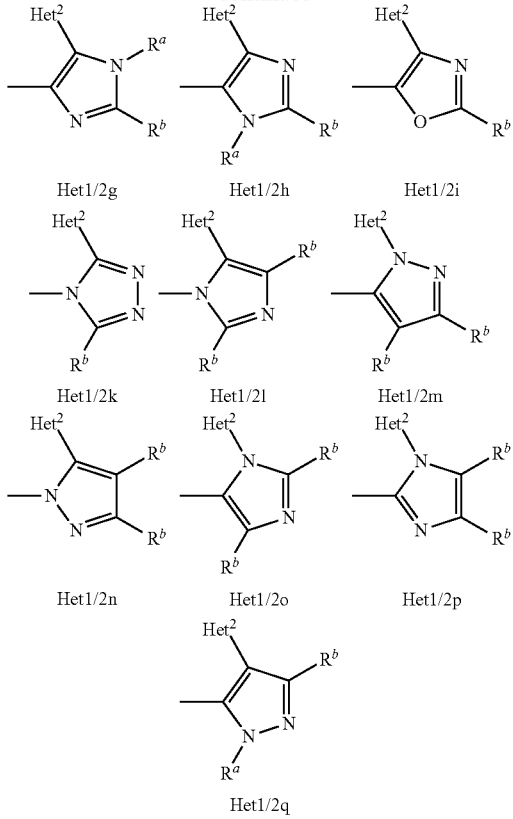

where $R^b$ is hydrogen or has one of the meanings given for R;

Het$^2$ is phenyl or a 5- or 6-membered monocyclic hetaryl, which has one heteroatom, selected from the group consisting of O, S and N as a ring member and optionally one or two further heteroatoms or heteroatom moieties independently selected from the group consisting of O, S, N and N—$R^{1a}$ as ring members, where phenyl and the 5- or 6 membered hetaryl are unsubstituted or carry, independently of each other, 1, 2 or 3, radicals $R^1$;

Cyc is selected from the group consisting of
  i. monocyclic 5-membered hetaryl having 1 or 2 nitrogen atoms and optionally a further heteroatom selected from the group consisting of O, S and N as ring members, which is unsubstituted or may carry 1, 2, 3 or 4 identical or different substituents $R^2$, or
  monocyclic 6-membered hetaryl, which is selected from the group consisting of 2-pyrimidinyl, 4-pyrimidinyl, 2-pyrazinyl, and 3-pyridazinyl, where the monocyclic 6-membered hetaryl is unsubstituted or may carry 1, 2, 3 or 4 identical or different substituents $R^2$,
  ii. fused 8-, 9- or 10-membered bicyclic hetaryl having one heteroatom selected from the group consisting of O, S and N and optionally 1, 2 or 3 nitrogen atoms as ring members, where the fused bicyclic hetaryl is selected from the group consisting of 3-isoquinolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, pyrrolo[2,3-b]pyridine-6-yl, thieno[3,2-b]pyridine-5-yl, imidazo-[2,1-b]- thiazol-6-yl, and 1,2,4-triazolo[1,5-a]pyridine-2-yl, where the fused bicyclic hetaryl is unsubstituted or may carry 1, 2, 3 or 4 identical or different substituents $R^2$, iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^{2a}$, and iv. $C_5$-$C_8$-cycloalkyl or saturated or partially unsaturated, 5- to 10-membered heteromonocyclic or heterobicyclic radical, having 1, 2 or 3 heteroatoms or heteroatom moieties independently selected from the group consisting of O, S, S=O, S(=O)$_2$, N and N—$R^{1a}$ as ring members, and which may carry 1, 2 or 3 identical or different substituents $R^{2b}$;

Ar is a radical of the following formula

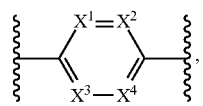

wherein
$X^1$ is N or C—$R^{x1}$;
$X^2$ is N or C—$R^{x2}$;
$X^3$ is N or C—$R^{x3}$;
$X^4$ is N or C—$R^{x4}$;
provided that 0, 1 or 2 of $X^1$, $X^2$, $X^3$ and $X^4$ are N;
and where $R^{x1}$, $R^{x2}$, $R^{x3}$, $R^{x4}$, independently of each other, are hydrogen or have one of the meanings given for $R^3$;

R is selected from the group consisting of halogen, CN, $NR^{13}R^{14}$, $C(O)NR^{13}R^{14}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $C_2$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^a$ is selected from the group consisting of hydrogen, $C(O)NR^{13}R^{14}$, $C_1$-$C_6$-alkyl, $C_2$-$C_6$-alkenyl, $C_2$-$C_6$-alkynyl, trimethylsilyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

two radicals R or the radical R together with the radical $R^a$, if attached to adjacent ring atoms, may also form a linear $C_3$-$C_5$-alkanediyl, wherein 1 or 2 CH$_2$ moieties can be replaced by C=O, O, S, S(=O), S(=O)$_2$ or NR', and where alkanediyl is unsubstituted or may carry 1 or 2 radicals independently selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy;

$R^1$ is attached to a carbon atom of Het$^2$ and selected from the group consisting of halogen, CN, $NR^{13}R^{14}$, $C(O)NR^{13}R^{14}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $C_2$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^{1a}$ is selected from the group consisting of hydrogen, $C(O)NR^{13}R^{14}$, $C_1$-$C_6$-alkyl, $C_2$-$C_6$-alkenyl, $C_2$-$C_6$-alkynyl, trimethylsilyl, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^2$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-$CO_2H$, $NR^{23}R^{24}$, $C(O)NR^{23}R^{24}$, $C_1$-$C_4$-alkyl-$NR^{23}R^{24}$, —$NR^{25}$—C(O)—$NR^{23}R^{24}$, $NR^{25}$—C(O)O—($C_1$-$C_4$-alkyl), —$NR^{25}$—$SO_2$—$R^{22}$, phenyl, CN, —$SF_5$, —$OSF_5$, —$SO_2R^{22}$, —$SR^{22}$, trimethylsilyl and $C_3$-$C_6$-cycloalkyl, where the cycloalkyl moiety in the last radical is unsubstituted, partially or completely fluorinated, or substituted by 1, 2 or 3 methyl groups, or two radicals $R^2$, which are bound to adjacent ring atoms may also form a linear $C_3$-$C_5$-alkanediyl, wherein 1 or 2 CH$_2$ moieties can be replaced by C=O, O, S, S(=O), S(=O)$_2$ or NR', and where alkanediyl is unsubstituted or may carry 1 or 2 radicals independently selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy;

$R^{2a}$ has one of the meanings given for $R^2$ or one radical $R^{2a}$ may also be a 5- or 6-membered hetaryl having 1 or 2 nitrogen atoms and optionally a further heteroatom selected from the group consisting of O, S and N as ring members, where hetaryl is unsubstituted or may carry 1, 2 or 3 radicals independently selected from the group consisting of halogen, OH, $C_1$-$C_4$-haloalkyl, $C_1$-$C_4$-alkoxy and $C_1$-$C_4$-haloalkoxy;

$R^{2b}$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, $C_1$-$C_4$-alkoxy-$C_1$-$C_4$-alkoxy, $C_1$-$C_4$-alkoxy-$C_1$-$C_4$-alkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-$CO_2H$, $NR^{23}R^{24}$, $C(O)NR^{23}R^{24}$, $C_1$-$C_4$-alkyl-$NR^{23}R^{24}$, —$NR^{25}$—C(O)—$NR^{23}R^{24}$, $NR^{25}$—C(O)O—($C_1$-$C_4$-alkyl), —$NR^{25}$—$SO_2$—$R^{22}$, phenyl, CN, —$SF_5$, —$OSF_5$, —$SO_2R^{22}$, —$SR^{22}$ and trimethylsilyl, or two radicals $R^{2a}$, which are bound to adjacent ring atoms may also form a fused benzene ring or a fused 5- or 6-membered heteroaromatic ring, having 1 ring member selected from the group consisting of O, S, N or NR' and optionally 1 or 2 further N-atoms as ring members, where the fused benzene or heteroaromatic ring is unsubstituted or may carry 1, 2, 3 or 4 radicals independently selected from the group consisting of halogen, OH, $C_1$-$C_4$-alkyl, $C_1$-$C_4$-fluoroalkyl, $C_1$-$C_4$-alkoxy and $C_1$-$C_4$-fluoroalkoxy;

$R^3$ independently of each other, are selected from the group consisting of halogen, CN, $NR^{33}R^{34}$, $C(O)NR^{33}R^{34}$, $C_1$-$C_6$-alkyl, $C_2$-$C_6$-alkenyl, $C_2$-$C_6$-alkynyl, trimethylsilyl, $C_1$-$C_6$-alkylsulfanyl, $C_1$-$C_6$-alkylsulfonyl, fluorinated $C_1$-$C_6$-alkylsulfanyl, fluorinated $C_1$-$C_6$-alkylsulfonyl, $C_1$-$C_4$-alkyl-$OR^{31}$, $C_1$-$C_4$-alkyl-$SR^{32}$, $C_1$-$C_4$-alkyl-$NR^{33}R^{34}$, $C_1$-$C_6$-alkoxy, $OC_1$-$C_4$-alkyl-$OR^{31}$, $OC_1$-$C_4$-alkyl-$SR^{32}$, $OC_1$-$C_4$-alkyl-$NR^{33}R^{34}$, $C_2$-$C_6$-alkenyloxy, $C_1$-$C_6$-fluoroalkyl, $C_1$-$C_6$-fluoroalkoxy, $C_3$-$C_6$-cycloalkyl and $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups;

$R^{11}$, and $R^{12}$ independently of each other are selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl, where $R^{11}$ may also be $C_1$-$C_4$-alkylsulfonyl or $C_1$-$C_4$-fluoroalkylsulfonyl;

$R^{13}$, and $R^{14}$ independently of each other are selected from the group consisting of hydrogen, $C_1$-$C_4$-alkyl, $C_1$-$C_4$-fluoroalkyl $C_3$-$C_6$-cycloalkyl and $C_3$-$C_6$-cycloalkyl-$C_1$-$C_4$-alkyl, or $R^{13}$ and $R^{14}$ together with the N atom to which they are attached form a 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 substituents independently selected from the group consisting of $C_1$-$C_4$-alkyl and fluorine;

$R^{22}$, $R^{31}$ and $R^{32}$ have one of the meanings given for $R^{11}$, or $R^{12}$;

$R^{23}$, $R^{24}$, $R^{33}$ and $R^{34}$ have one of the meanings given for $R^{13}$, or $R^{14}$;

$R^{25}$ is selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl; and R' is selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl.

2. The compound of claim 1, where both $Y^1$ and $Y^2$ in $Het^1$ are carbon atoms.

3. The compound of claim 1, where $Het^1$ is selected from the group consisting of 1-($R^a$)-1H-pyrazole-3,4-diyl, 1-($R^a$)-1H-pyrazole-4,5-diyl, 1H-pyrazole-1,5-diyl, 1-($R^a$)-1H-imidazol-4,5-diyl, isoxazol-4,5-diyl, isoxazol-4,5-diyl, 1-($R^a$)-1H-1,2,3-triazol-4,5-diyl, 1H-oxazol-4,5-diyl, 1H-imidazol-1,2-diyl, 1H-imidazol-1,5-diyl and 1H-1,3,4-triazol-1,2-diyl.

4. The compound of claim 1, where Het1/2 is a radical Het1/2a.

5. The compound of claim 1, where $R^b$ in radicals Het1/2a to Het1/2q is hydrogen.

6. The compound of claim 1, where $X^1$ is C—$R^{x1}$, $X^2$ is C—$R^{x2}$, $X^3$ is C—$R^{x3}$ and $X^4$ is C—$R^{x4}$, where $R^{x1}$, $R^{x2}$, $R^{x3}$, $R^{x4}$, independently of each other, are hydrogen or have one of the meanings given for $R^3$, and at least 3 of $R^{x1}$, $R^{x2}$, $R^{x3}$ and $R^{x4}$ are hydrogen and at most one of $R^{x1}$, $R^{x2}$, $R^{x3}$ and $R^{x4}$ is a radical $R^3$.

7. The compound of claim 1, where each $X^1$, $X^2$, $X^3$ and $X^4$ is CH.

8. The compound of claim 1, which is of formula (I-A):

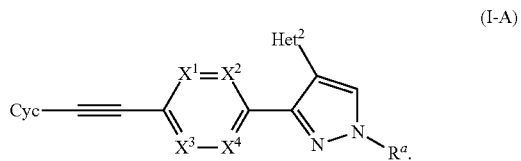

9. The compound of claim 1, which is of formula (I-A.a):

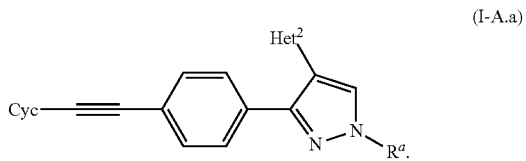

10. The compound of claim 1, where $R^a$ is selected from the group consisting of $C_1$-$C_4$-alkyl and $C_1$-$C_4$-fluoroalkyl.

11. The compound of claim 1, where $Het^2$ is phenyl or a 5- or 6-membered monocyclic hetaryl, which has one heteroatom, selected from the group consisting of O, S and N as a ring member and optionally one or two further heteroatoms or heteroatom moieties independently selected from the group consisting of O, S, N and N—$R^{1a}$ as ring members, where phenyl and the 5- or 6 membered hetaryl are unsubstituted or carry, independently of each other, 1, 2 or 3, radicals $R^1$.

12. The compound of claim 1, where $Het^2$ is selected from the group consisting of phenyl, oxazolyl, isoxazolyl, furyl, thienyl, pyrrolyl, imidazolyl, pyrazolyl, pyridyl, pyrimidinyl and pyridazinyl, where the aforementioned radicals are unsubstituted or may carry 1, 2 or 3 radicals $R^1$, where each $R^1$ is independently selected from the group consisting of fluorine, chlorine, CN, methyl, difluoromethyl, trifluoromethyl, methoxy, difluoromethoxy, trifluoromethoxy and $NH_2$.

13. The compound of claim 1, where $Het^2$ is 4-pyridyl.

14. The compound of claim 1, which is of formula (I-A.a'):

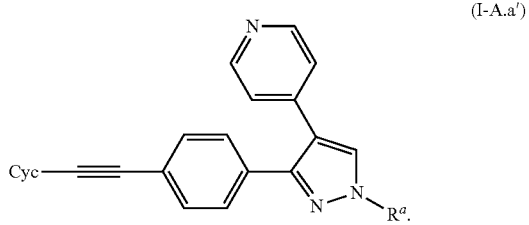

15. The compound of claim 1, where Cyc is selected from the group consisting of C-bound 5- or 6-membered monocyclic hetaryl, which has 1 or 2 nitrogen atoms as ring members, and C-bound, 9- or 10-membered fused bicyclic hetaryl, which has 1 or 2 nitrogen atoms as ring members and optionally a further heteroatom selected from the group consisting of O, S and N as ring member;

where monocyclic hetaryl, benzofuryl and bicyclic hetaryl may be unsubstituted or may carry 1, 2, 3 or 4 substituents $R^2$.

16. The compound of claim 15, where Cyc has at least one imino-nitrogen as ring member, which is located in the position adjacent to the carbon atom which is bound to the triple bond.

17. The compound of claim 16, where Cyc is selected from the group consisting of 2-pyrimidinyl, 2-pyrazinyl, 3-pyridazinyl, 2-imidazolyl, 4-imidazolyl, 3-pyrazolyl, 2-thiazolyl, 4-thiazolyl, 3-isoquinolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, pyrrolo[2,3-b]pyridine-6-yl, thieno[3,2-b]pyridine-5-yl, imidazo-[2,1-b]-thiazol-6-yl and 1,2,4-triazolo[1,5-a]pyridine-2-yl, where the aforementioned radicals may carry 1, 2 or 3 radicals independently selected from the group consisting of fluorine, chlorine, methyl; fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

18. The compound of claim 1, which is selected from the group consisting of:
- 4-(1-methyl-3-(4-((1-methyl-1H-imidazol-5-yl)ethynyl)phenyl)-1H-pyrazole-4-yl)pyridine;
- 4-(1-methyl-3-(4-((1-propyl-1H-pyrazol-4-yl)ethynyl)phenyl)-1H-pyrazole-4-yl)pyri din e;
- 4-(1-methyl-3-(4-((1-methyl-1H-imidazol-2-yl)ethynyl)phenyl)-1H-pyrazole-4-yl)pyridine;
- 4-(1-methyl-3-(4-((1-methyl-1H-pyrazol-4-yl)ethynyl)phenyl)-1H-pyrazole-4-yl)pyridine;
- 4-(3-(4-(((1H-pyrazol-4-yl)ethynyl)phenyl)-1-methyl-1H-pyrazole-4-yl)pyridine;
- 2-[2-[4-[1-methyl-4-(4-pyridyl)pyrazol-3-yl]phenyl]ethynyl]-1,5-naphthyridine;
- 2-[2-[4-[1-methyl-4-(4-pyridyl)pyrazol-3-yl]phenyl]ethynyl]imidazo[1,2-a]pyridine;
- 6-[2-[4-[1-methyl-4-(4-pyridyl)pyrazol-3-yl]phenyl]ethynyl]-1H-pyrrolo[2,3-b]pyridine;
- 2-[2-[4-[1-methyl-4-(4-pyridyl)pyrazol-3-yl]phenyl]ethynyl]thiazole; and
- 2-[2-[4-[1-methyl-4-(4-pyridyl)pyrazol-3-yl]phenyl]ethynyl]quinoxaline;

or a pharmaceutically acceptable salt thereof.

19. The compound of claim 1, for use in therapy.

20. A pharmaceutical composition which comprises at least one compound as claimed in claim 1 and at least one excipient.

21. The compound of claim 1, which comprises an isotope label.

22. The compound of claim 21, where the radical $R^3$ or the radical $R^a$ comprises the isotope label.

23. The compound of claim 21, where the isotope label is a positron emitting isotope or a gamma ray emitting isotope.

24. A method for performing positron emission tomography or single photon emission computed tomography, the method comprising using the compound of claim 23.

25. A method for performing positron emission tomography or single photon emission computed tomography of the brain, the method comprising using the compound of claim 23.

26. The compound of claim 21, where the isotope label is a $^{11}$C-label, a $^{18}$F-label, or a $^{123}$I label.

* * * * *